(12) United States Patent
Giles et al.

(10) Patent No.: US 12,124,769 B2
(45) Date of Patent: Oct. 22, 2024

(54) ACTIVITY-DEPENDENT AUDIO FEEDBACK THEMES FOR TOUCH GESTURE INPUTS

(71) Applicant: Google LLC, Mountain View, CA (US)

(72) Inventors: Daniel Lee Giles, Fremont, CA (US); Abidshan Jeffrey Nassar, San Francisco, CA (US)

(73) Assignee: GOOGLE LLC, Mountain View, CA (US)

( * ) Notice: Subject to any disclaimer, the term of this patent is extended or adjusted under 35 U.S.C. 154(b) by 26 days.

(21) Appl. No.: 18/164,694

(22) Filed: Feb. 6, 2023

(65) Prior Publication Data

US 2023/0297330 A1 Sep. 21, 2023

Related U.S. Application Data

(63) Continuation of application No. 17/364,023, filed on Jun. 30, 2021, now Pat. No. 11,573,762.

(51) Int. Cl.
| | |
|---|---|
| *G06F 3/048* | (2013.01) |
| *A61B 5/11* | (2006.01) |
| *G06F 3/01* | (2006.01) |
| *G06F 3/041* | (2006.01) |
| *G06F 3/0488* | (2022.01) |
| *G06F 3/16* | (2006.01) |

(52) U.S. Cl.
CPC ............ *G06F 3/167* (2013.01); *A61B 5/1118* (2013.01); *G06F 3/016* (2013.01); *G06F 3/04164* (2019.05); *G06F 3/0488* (2013.01); *G06F 3/165* (2013.01)

(58) Field of Classification Search
CPC .......... G03F 3/011; G03F 3/016; G03F 3/017; G03F 3/165; G03F 3/167; G03F 3/04164; G03F 3/0488
See application file for complete search history.

(56) References Cited

U.S. PATENT DOCUMENTS

| | | | |
|---|---|---|---|
| 2009/0278809 A1 | 11/2009 | Ohsawa | |
| 2010/0085169 A1* | 4/2010 | Poupyrev | ............ G06F 3/04886 345/174 |
| 2010/0317371 A1* | 12/2010 | Westerinen | ....... H04M 1/72451 455/456.6 |
| 2013/0265226 A1* | 10/2013 | Park | ........................ G06F 3/017 345/156 |

(Continued)

FOREIGN PATENT DOCUMENTS

| | | |
|---|---|---|
| WO | WO2011100441 | 8/2011 |
| WO | WO2018200798 | 11/2018 |
| WO | WO2019204596 | 10/2019 |

*Primary Examiner* — Claudia Dragoescu
(74) *Attorney, Agent, or Firm* — DORITY & MANNING P.A.

(57) ABSTRACT

Systems and methods that provide audio feedback in response to gesture validity can provide a more intuitive interface that can train users to correctly complete gestures. Moreover, systems and methods that provide line-specific audio feedback can provide more specific feedback that can allow a user to better understand what sensing line is being contacted. The systems and methods can further include basing the audio feedback based at least in part on obtained activity data, such that invalid and valid feedbacks can provide different sounds dependent on the determined activity state.

19 Claims, 19 Drawing Sheets

(56) References Cited

U.S. PATENT DOCUMENTS

| | | | |
|---|---|---|---|
| 2014/0092032 A1* | 4/2014 | Moore | G06F 3/04883 |
| | | | 345/173 |
| 2016/0283101 A1* | 9/2016 | Schwesig | D03D 1/0088 |
| 2017/0228009 A1 | 8/2017 | Chueh et al. | |
| 2018/0307315 A1* | 10/2018 | Gong | G06F 3/044 |
| 2020/0229515 A1 | 7/2020 | Poupyrev et al. | |

* cited by examiner

ACTIVITY-DEPENDENT AUDIO FEEDBACK THEMES FOR TOUCH GESTURE INPUTS

PRIORITY CLAIM

The present application is a continuation of U.S. application Ser. No. 17/364,023 having a filing date of Jun. 30, 2021. U.S. application Ser. No. 17/364,023 is hereby incorporated by reference in its entirety.

FIELD

The present disclosure relates generally to providing audio feedback in response to a touch input. More particularly, the present disclosure relates to receiving activity data and touch gesture input data and determining an audio feedback based on the activity data and the gesture's validity.

BACKGROUND

Touch based ambient devices which use gestures as an input mechanism require accurate motions from users to ensure accurate gesture recognition. Gestures performed by users however, have a great degree of variability, which can make it very difficult for the machine learning algorithms to recognize the user's intent. Even with visual or haptic feedback users may still be confused as to what is an acceptable versus what is an unacceptable gesture. This leads to reduced recognition rates during runtime, and higher frustration by users.

Moreover, inputs can be limited for some devices, and devices may fail to leverage activity dependent data for different inputs, which can further restrict the corpus of inputs available.

SUMMARY

Aspects and advantages of embodiments of the present disclosure will be set forth in part in the following description, or can be learned from the description, or can be learned through practice of the embodiments.

One example aspect of the present disclosure is directed to a computing system for an interactive object. The system can include an input sensor, one or more activity sensors configured to generate activity data associated with user activity, and one or more control circuits configured to perform operations. The operations can include obtain input data associated with at least one input detected by the input sensor. The operations can include determine an activity state of the user based at least in part on the activity data generated by the one or more activity sensors. In some implementations, the operations can include determine a gesture validity associated with the at least one input detected by the input sensor. The operations can include determine an audio feedback based at least in part on the activity state and the gesture validity. The system can include one or more audio output devices configured to provide the audio feedback based at least in part on the activity state and the gesture validity.

Another example aspect of the present disclosure is directed to a computer-implemented method. The method can include detecting, by a computing system including one or more processors, a respective response associated with each of a plurality of parallel sensing lines of a touch sensor in response to at least one touch input. The method can include determining, by the computing system, a line-specific audio feedback for each sensing line associated with the touch input. The method can include sending, by the computing system, a first set of instructions to an audio output device to provide the line-specific audio feedback. The method can include determining, by the computing system, whether the touch input can be associated with at least one of a plurality of actions. In some implementations, the method can include sending, by the computing system, a second set of instructions to the audio output device to provide a gesture audio feedback if the touch input can be associated with at least one of the plurality of actions.

Another example aspect of the present disclosure is directed to an interactive object. The interactive object can include an article having one or more touch sensors integrated therein for recognizing a user gestural input and an electronic device associated with the article, the electronic device can be communicatively coupled to the one or more touch sensors of the article. The electronic device can have a processor and an audio output device capable of providing audio feedback to the user. The interactive object can include one or more contextual activity sensors associated with at least one of the article or the electronic device. The one or more contextual activity sensors can include at least one of an inertial motion sensor, a location sensor, a proximity sensor, or other type of sensor. In some implementations, the electronic device can be configured and programmed to perform operations. The operations can include process readings from the one or more contextual activity sensors to determine which of a predetermined plurality of user activities the user is performing. During a first time interval in which the user is determined to be performing a first activity, the operations can include receiving a first touch gesture from the user; determining whether the first touch gesture is valid or invalid; and providing first audio feedback of a first sound category to the user. In some implementations, the first audio feedback can include a first sound if the first touch gesture is valid and can include a second sound if the first touch gesture is invalid. During a second time interval in which the user is determined to be performing a second activity different than the first activity, the operations can include receiving a second touch gesture from the user; determining whether the second touch gesture is valid or invalid; and providing second audio feedback of a second sound category to the user. The second sound category can be different than said first sound category. In some implementations, the second audio feedback can include a third sound if the second touch gesture is valid and can include a fourth sound if the second touch gesture is invalid. In some implementations, the user can be provided with audio feedback sounds that, in addition to confirming whether their touch gestures are valid, also provide confirmation of which activity the user has been determined to be performing.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1:
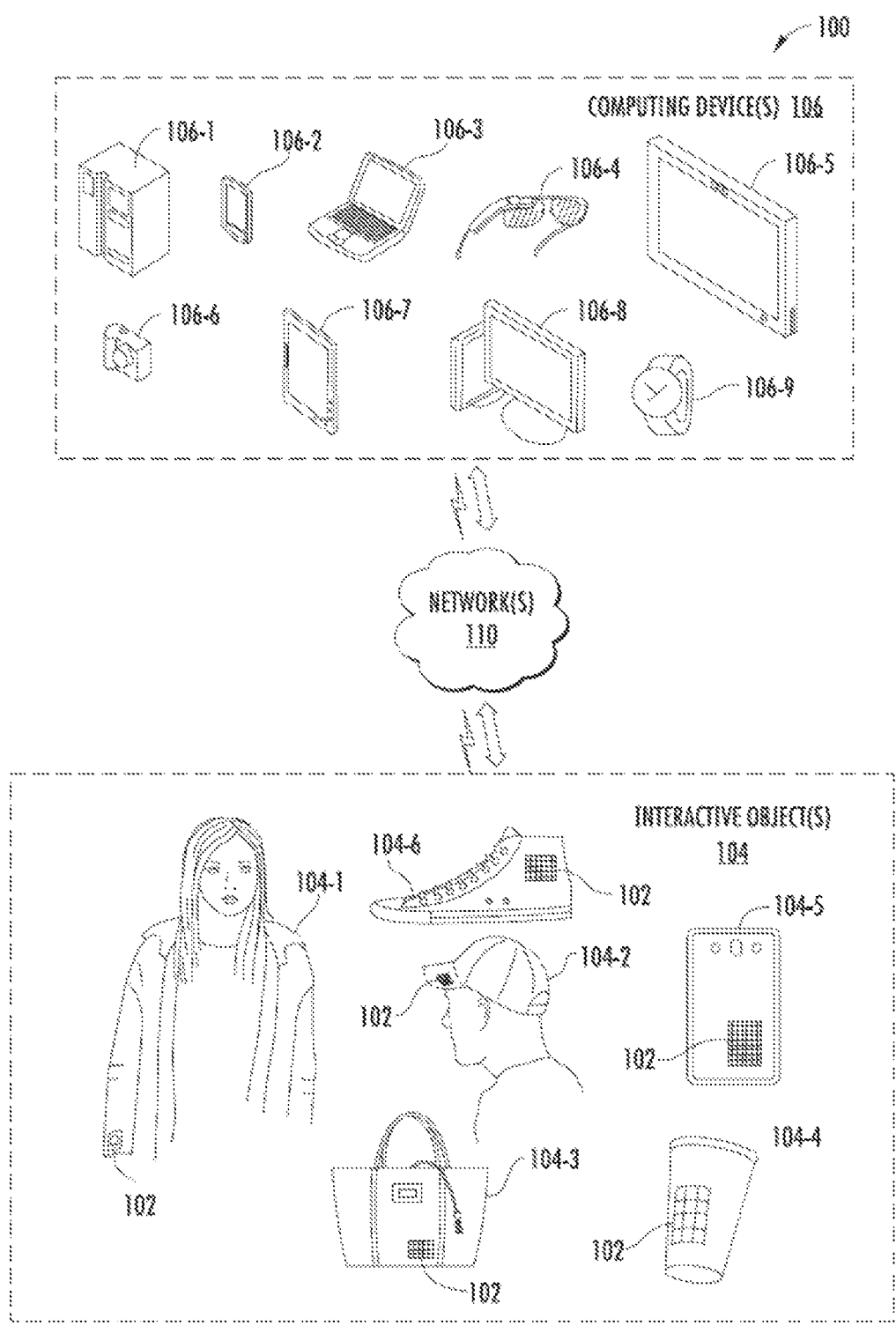
FIG. 1 illustrates an example computing environment including an interactive object having a touch sensor in accordance with example embodiments of the present disclosure.

Reference numerals that are repeated across plural figures are intended to identify the same features in various implementations.

DETAILED DESCRIPTION

Generally, the present disclosure relates to systems and methods for providing feedback in response to inputs. For example, a computing system can include a plurality of sensors, which may include one or more activity sensors and one or more input sensors (e.g., touch sensors). The one or more activity sensors can be configured to generate activity data descriptive of a user's activity state, and the one or more touch sensors can include a plurality of sensing lines configured to receive touch inputs. The activity data can be processed to determine the activity state (e.g., a user is at a high activity level, a user is at a low activity level, a user is at home, a user is at work, a user is listening to music, a user is commuting, etc.), which can then be used to determine a plurality of functions, or actions, associated with that activity state. The plurality of functions, or actions (e.g., next song, volume up, call another device, turn on, turn off, etc.), can be associated with a plurality of gestures for selection (e.g., a swipe up, a swipe down, touching a first line and a third line, etc.). The systems and methods can then process the touch input to determine if the touch input is associated with any of the plurality of gestures for the plurality of functions. An audio feedback can then be determined and provided based on the activity state and whether the touch input matches one or more of the plurality of gestures. For example, if a user is determined to be at a high activity level the sound provided can be different than the possible sounds provided when a user is at a low activity level. Moreover, if the touch input is determined to match one or more of the plurality of gestures, the sound provided can be different than the sound provided if the touch input does not match one of the plurality of gestures. In some implementations, if there is not a match, no sound may be played or may cause haptic feedback to occur.

The systems and methods in accordance with example implementations can provide for interface training and input acknowledgement. For example, the systems and methods can further include line-specific audio feedback for training a user to input gestures for selecting functions. More specifically, the line-specific audio feedback can provide a user with a notification to inform which sensing lines are being contacted. After completion of the gesture, a notification can be provided to inform the user if the gesture is valid or invalid, such that a valid gesture is a gesture that matches one or more of the plurality of gestures associated with the plurality of functions. In some implementations, the notifications can differ based on which activity state the user is determined to be in. Additionally and/or alternatively, an audio notification can be provided to indicate the activity state is determined to have changed (e.g., a change in activity level or a change in location).

Generally, the present disclosure is directed to audio feedback in response to touch gesture inputs. More specifically, the systems and methods disclosed herein can receive a gesture input, process the gesture input to determine if the gesture input is associated with any actions, and provide audio feedback based at least in part on the determination. For example, a user can be wearing a smart wearable with a plurality of conductive lines that form one or more capacitive-array touch sensors. The user can swipe down on the lines to input a down swipe gesture. The systems and methods can process the touch gesture and determine if there is a programmed action associated with the down gesture. If there is a determined associated action, a first sound can be played, and if there is not, a second sound can play. If there is a determined associated action with a gesture or touch input, the gesture or touch input may be determined to be valid. If there is not a determined action associated with a gesture or touch input, the gesture or touch input may be determined to be invalid. In some examples, a gesture may be determined to be valid if the gesture is part of a set of predefined gestures. If a gesture is not part of a set of predefined gestures, the gesture may be determined to be invalid.

Moreover, determining the action can be based at least in part on a user's activity or situation (e.g., a commute bundle, a workout bundle, a work bundle, etc.). The smart wearable or soft goods item can include different corpus of actions for different user activities or situations. For example, the system can include one or more inertial sensors, which can be used to determine movement by a user. If a user is determined to be in an active state, the system can have a set of actions that can differ from if the user is determined to be in an inactive state. For example, a lateral swipe during an active state can be associated with a burnt calories function that can provide feedback on a determined amount of calories burnt, while a lateral function during an inactive state can be associated with a weather function that can provide feedback on the weather forecast for the day.

Alternatively and/or additionally, the systems and methods can have different sounds dependent on the user activity or situation. For example, if a user is determined to be working out, the audio feedback may be a first sound for a valid gesture, and the audio feedback can be a second sound for an invalid gesture. However, if the user is determined to be in a relaxation state or low activity state, the audio feedback may be a third sound for a valid gesture, and the audio feedback may be a fourth sound or no sound at all for an invalid gesture.

The valid-invalid audio feedback can provide a more intuitive input interface. Alternatively and/or additionally, the system can provide different sounds for each sensor or sensor set. For example, one sensor set can provide a chime feedback, while another sensor set can provide a ding feedback. The varying sounds for each sensor or sensor set can allow a user to better understand which sensor or sensor set they are coming into contact with, which can provide a more intuitive interface. The different sounds can provide quicker feedback to in turn potentially lead to quicker training of successful gestures. In this implementation, the system can point the user more accurately to exactly where their gesture fell out of recognition. In some implementations, the touch sensors can be arranged in a similar way to strings on a guitar with thin parallel lines of sensor lines. In some implementations, the system can have multiple layers of "string sensors" for layered input or for cancelling out input noise. Moreover, in some implementations, the system can have one or more perpendicular lines of touch sensors for receiving more complex gesture inputs.

In some implementations, each string can provide a separate sound but may be complementary to one another, similar to strings on a guitar, such that a full swipe can provide a combination of complementary sounds to provide a pleasing combined tone.

Moreover, in some implementations, the system can provide an audio feedback for each string separately and at the end of the gesture can provide an output indicating a successful gesture if the gesture was determined to be valid or no sound at all if the gesture was determined to be invalid.

In some implementations, the audio feedback can be a form of gesture training for a user to help a user get familiar with different gesture inputs. The valid sounds and invalid sounds can reinforce valid gestures and deter invalid gestures and can therefore train the user to more accurately complete gestures. After learning how to make the valid inputs, the user may turn off the audio feedback.

In some implementations, the systems and methods can include a computing system. The computing system can include an input sensor, one or more activity sensors, one or more control circuits, and one or more audio output devices. In some implementations, the input sensor can include one or more touch sensors. The touch sensor can include a plurality of conductive sensing elements integrated with a flexible substrate. In some implementations, the plurality of conductive sensing elements can be of cylindrical shape. The one or more activity sensors can be configured to generate activity data descriptive of an activity state of a user. In some implementations, the one or more activity sensors can include at least one of an inertial sensor, a location sensor, or a proximity sensor. The one or more control circuits can be configured to obtain input data associated with an input to the input sensor. In some implementations, the input data can be touch data associated with a touch input to a touch sensor. The touch data being based at least in part on a respective response to the touch input by the plurality of conductive sensing elements. Additionally and/or alternatively, the one or more control circuits can be configured to determine the activity state of the user based at least in part on activity data generated by the one or more activity sensors. Moreover, the one or more control circuits can be configured to determine a gesture validity based on whether the touch input is associated with an action and determine an audio feedback based at least in part on the activity state and the gesture validity. In some implementations, determining the gesture validity can include determining a plurality of actions associated with the activity state and determining the gesture validity based on whether the touch input is associated with at least one action of the plurality of actions. In some implementations, the one or more audio output devices can be configured to provide a plurality of sounds based on the activity state and the gesture validity. The one or more audio output devices can include at least one of a mobile computing device or communicatively connected to a mobile computing device. The plurality of sounds can include a plurality of musical sounds descriptive of sounds output by a musical instrument.

In some implementations, the one or more control circuits can be configured to determine an action associated with the touch input, and the sensor system can include one or more communication components configured to send instructions to a computing device to complete the action. Additionally, in some implementations, determining a gesture validity can include determining whether the touch input is indicative of one or more predefined gestures.

Alternatively and/or additionally, the systems and methods for training a user to provide inputs to the interface can include an interactive object wearable by a user. The interactive object can include a touch sensor and one or more control circuits. The touch sensor can be implemented into the sleeve of a wearable garment. In some implementations, the touch sensor can include a plurality of parallel sensing lines elongated in one or more directions with a separation therebetween. The touch sensor can include an input surface configured to receive inputs from the user. The one or more control circuits can be in communication with the touch sensor, and the one or more control circuits can be configured to perform one or more operations. The operations can include detecting a respective response associated with each of the plurality of parallel sensing lines in response to a touch input to the touch sensor. The operations can further include determining a line-specific audio feedback for each sensing line associated with the touch input. A first set of instructions can then be sent. The first set of instructions can include instructions to an audio output device to play the line-specific audio feedback. In some implementations, the line-specific audio feedback for each sensing line can include a different sound frequency but be of a common musical note. The operations can include determining whether the touch input is associated with at least one of a plurality of actions. A second set of instructions can then be sent. The second set of instructions can include instructions to the audio output device to play a first sound if the touch input is associated with at least one of the plurality of actions. The second set of instructions can include at least one of play a second sound if the touch input is not associated with at least one of the plurality of actions or provide haptic feedback if the touch input is not associated with at least one of the plurality of actions.

In some implementations, the interactive object can include a second plurality of parallel sensing lines elongated in perpendicular direction to the plurality of parallel sensing lines. Moreover, in some implementations, in response to determining the touch input is associated with at least one of the plurality of actions, action instructions can be sent to a computing device to complete the action. The audio output device and the interactive object can be communicatively paired via Bluetooth. In some implementations, the audio output device can be a mobile computing device or may be communicatively connected to a mobile computing device.

Additionally, the operations can include determining a user activity state changes from a first activity state to a second activity state; determining an activity state sound associated with the second activity state; and sending activity state instructions to the audio output device to play the activity state sound.

In some implementations, the interactive object wearable can include a smart wearable device. In some implementations, the one or more activity sensors can be configured to generate activity data descriptive of an activity state. Moreover, the smart wearable device can include one or more touch sensors configured to generate gesture data in response to receiving touch input. The smart wearable device may include one or more processors. The one or more processors can be configured to process the activity data generated by the one or more activity sensors to determine the activity state and determine a plurality of actions associated with that particular activity state. Moreover, the operations can include processing the gesture data to determine a touch input validity. Determining the touch input validity can include determining whether the touch inputs are valid or invalid. Valid touch inputs can include a valid gesture associated with at least one of the plurality of actions. Invalid touch inputs can include an invalid gesture that is not associated with any of the plurality of actions. The one or more processors can be configured to determine an audio feedback based at least in part on the activity state and touch input validity.

The smart wearable device can further include one or more communication components configured to send instructions to one or more computing devices based at least in part on the gesture data and the touch input validity.

The one or more activity sensors can include various sensor types for intaking various data types associated with various possible activities. For example, the one or more activity sensors can include a clock and the activity state can be based on a time of day. Alternatively and/or additionally, the one or more activity sensors can include an inertial sensor, and the activity state can be based on a user's determined activity level. In some implementations, the one or more activity sensors can include a proximity sensor, and the activity state can be based at least in part on a proximity to one or more other devices or objects. The one or more activity sensors may include a location sensor, and the activity state can be based at least in part on a location of the smart wearable device.

In some implementations, the systems and methods disclosed herein can be implemented in a computing system. The computing system can include an article having one or more touch sensors integrated therein for recognizing a user gestural input. The computing system may further include an electronic device associated with the article. The electronic device can be communicatively coupled to the gesture sensor of the article. Moreover, the electronic device can have a processor and an audio output device capable of providing audio feedback to the user. In some implementations, the electronic device can include a visual display for displaying a visualization of the one or more touch sensors.

The computing system can further include one or more contextual activity sensors associated with at least one of the article or the electronic device. The one or more contextual activity sensors can include at least one of an inertial motion sensor, a location sensor, a proximity sensor, or another type of sensor.

In some implementations, the electronic device can be configured and programmed to perform operations stored in one or more non-transitory computer readable media. The operations can include processing readings from the one or more contextual activity sensors to determine which of a predetermined plurality of user activities the user is performing. The predetermined plurality of user activities can include a relaxing activity and a working out activity.

During a first time interval in which the user is determined to be performing a first activity, the operations can include receiving a first touch gesture from the user and determining whether the first touch gesture is valid or invalid. The first touch gesture can include one or more directions and one or more magnitudes for each respective direction. A first audio feedback of a first sound category can then be provided to the user. The first audio feedback can include a first sound if the first touch gesture is valid and can include a second sound if the first touch gesture is invalid. In some implementations, the first activity can be at least one of the relaxing activity or working out activity. The visual display on the electronic device may display the visualization with a representation of the first touch gesture in response to receiving the first touch gesture from the user.

During a second time interval in which the user is determined to be performing a second activity different than the first activity, the operations can include receiving a second touch gesture from the user and determining whether the second touch gesture is valid or invalid. The second touch gesture can include one or more directions and one or more magnitudes for each respective direction. A second audio feedback of a second sound category can then be provided to the user. The second sound category can be different than said first sound category. In some implementations, the second audio feedback can include a third sound if the second touch gesture is valid and can include a fourth sound if the second touch gesture is invalid.

The audio feedback sounds can be provided to confirm whether the touch gestures are valid and provide confirmation of which activity the user has been determined to be performing.

The article can be a variety of clothing types, accessories, or other objects. For example, the article can be a jacket, and the one or more touch sensors can be in the sleeve of the jacket. Alternatively, the article can be a carrying device, and the one or more touch sensors can be in a strap of the carrying device.

Alternatively and/or additionally, the systems and methods can include generating activity data descriptive of a user activity with one or more activity sensors. The systems and methods can include generating input data descriptive of one or more user inputs with one or more touch sensors. In some implementations, the systems and methods can include determining the user activity based at least in part on the activity data. In some implementations, the user activity can be determined based at least in part on one of a user's location, a user's physical activity level, and/or a time of day. A plurality of actions associated with the user activity can be determined. In some implementations, the plurality of actions associated with the user activity can differ from a second plurality of actions associated with a second user activity. The input data and the plurality of actions can be processed to determine an audio feedback. If the input data is associated with at least one of the plurality of actions, the audio feedback can include a first sound, and if the input data is not associated with at least one of the plurality of actions, the audio feedback can include a second sound.

The systems and methods can further include sending, by one or more wireless transmission components, instructions to play the audio feedback. Alternatively and/or additionally, the systems and methods can include generating, by the one or more activity sensors, second activity data descriptive of a second user activity and generating, by the one or more touch sensors, second input data descriptive of one or more second user inputs. The systems and methods can include determining the second user activity based at least in part on the second activity data. A second plurality of actions associated with the second user activity can be determined. Moreover, a second audio feedback can be determined based on the second input data and the second plurality of actions. If the second input data is associated with at least one of the second plurality of actions, the second audio feedback can include a third sound.

In some implementations, the systems and methods can include processing the input data to determine one or more string sensors contacted during user input. The systems and methods can then include determining an audio response for each respective string sensor of the one or more string sensors and sending, by one or more wireless transmission components, instructions to play the one or more audio responses.

The one or more user inputs can be one or more gesture inputs descriptive of one or more interactions with one or more string sensors.

The systems and methods can further include determining an activity feedback associated with the user activity and sending, by one or more communication components, instructions to provide the activity feedback in response to determining the user activity.

In some implementations, the systems and methods disclosed herein can utilize one or more machine-learned models for activity state determination. More specifically, one or more machine-learned models may be trained to learn when different action sets and their respective gesture sets should be used. For example, one or more machine-learned models can be used to determine when a specific user has gone from an inactive state to an active state. Another example can involve training a machine-learned model to determine what actions are commonly taken at certain times of day or at certain locations. The action sets can then be associated with certain gestures and can be associated with an activity state and an activity state audio feedback set.

One example implementation of systems and methods disclosed herein can include a user wearing a smart jacket. A user can be wearing a jacket, which can contain a touch gesture sensor on its sleeve, and which can be coupled to a smartphone. The smartphone can be playing music to the user over headphones. During a first time interval, the user can be sitting quietly in a library, and they make a down-swipe gesture on the sleeve of their jacket that is intended to make the smartphone advance to the next song. If the gesture was done properly, a nice brief soft harmonious sound of a classical violin can be played. If the gesture was not done properly, the classical violin can play a soft, discordant, uncomfortable-sounding violin sound. During a second time interval, the user can be jogging or lifting weights, and the user can make a down-swipe gesture that can be intended to advance the music to the next song. If the gesture was done properly, a brief loud but harmonious sound of an aggressive rock-n-roll electric guitar can be played. If the gesture was not done properly, then a loud, discordant, uncomfortable aggressive sound of a rock-n-roll electric guitar can be played. Thus, the kind of sound which the user hears for gestural input feedback can be customized to the sensed activity of the user (e.g., soft and classy for when the user is in a library reading, and loud and aggressive if the user is jogging or lifting weights).

The systems and methods disclosed herein can enable for a large corpus of actions to be selected despite limited inputs being available. The systems and methods can leverage determining an activity state to provide gesture sets associated with action sets dependent on a determined activity, such that a user can be provided access to actions they commonly select during certain activity states. For example, the systems and methods may determine that a user uses a certain set of actions often at home and a different set of actions at work; therefore, the systems and methods can associate action sets with their respective activity state (i.e., respective locations), such that gestures at each location result in different action selections.

Additionally and/or alternatively, a user may manually define activity states, action sets for activity states, and/or gestures for action sets for specific activity states. The manually defined action sets can provide a tailored input experience that leverages activity state determination to add more accessibility to actions for selection despite limited input possibilities.

The touch inputs can include a variety of inputs. Additionally, the sensing lines of the one or more touch sensors can be configured in a variety of layouts. For example, the touch inputs can be one or more compressions of the sensing lines individually or in combination. Alternatively, a touch input can include swiping across multiple sensing lines in one or more directions. In some implementations, some sensing lines may be configured to receive gestures in a parallel gesture to at least a portion of the sensing lines. This implementation can involve perpendicular sensing lines or may involve having a portion of a set of sensing lines being disposed for input in a staggered manner. In some implementations, the duration of the compressions or gestures can indicate differing intents and, therefore, can be interpreted as different inputs. Moreover, in some implementations, the pressure provided can indicate an intent of the touch input. In some implementations, a gesture may be restricted to a time period such that if a user does not complete the touch input, or gesture, in a defined amount of time, the gesture will be determined invalid.

The systems and methods disclosed herein can be used for providing audio feedback for a variety of input types. For example, in some implementations, the systems and methods can include obtaining input data descriptive of motion from one or more motion sensors (e.g., one or more inertial sensors). The motion data can be processed to determine if the motion is indicative of an input (e.g., an arm extension, a leg motion, a pointing pose, etc.) matching at least one of the plurality of gestures associated with the plurality of actions.

Alternatively and/or additionally, the input can be an input detected using one or more image sensors. For example, the input may be a wave, an eye motion, blinking, etc. Therefore, the input data can comprise image data that can be analyzed to determine if the input is associated with one or more gestures from the plurality of gestures associated with the plurality of actions for a specific activity state.

In some implementations, the input can be a speech input detected using one or more audio sensors. For example, the systems and methods disclosed herein can include one or more models for processing the audio data to generate speech recognition outputs, which can then be analyzed to determine if the input is associated with one or more gestures from the plurality of gestures.

In some implementations, the systems and methods disclosed herein can be provided as part of a game used for training or reinforcement of gesture inputs, such that a user may select a tutorial or game in order to implement the systems and methods disclosed herein.

In some implementations, the audio feedbacks can be determined based on sound mapping in a database of sounds, such that each line, each gesture, and each activity state can be mapped to one or more sounds in a database of sounds. The sounds can be synthetically created sounds, recorded sounds, or sounds downloaded from another database. The database can include a plurality of harmonious sounds and a plurality of discordant sounds for providing harmonious sounds with a valid input and a discordant sound for invalid inputs.

The systems and methods disclosed herein can be implemented in a variety of methods and systems, including, but not limited to: computer-implemented methods, computing systems, sensor systems, computing devices, interactive objects, and/or wearable devices.

The systems and methods of the present disclosure provide a number of technical effects and benefits. As one example, the system and methods can provide a more intuitive interface by providing audio feedback with respect to an activity state and a gesture validity. The systems and methods can be used to train a user how to correctly complete gestures. The systems and methods can further be used to inform a user what specific sensing lines are contacted and in what order. Furthermore, the systems and methods can enable activity state and gesture validity audio feedback that can inform a user what action set is currently active and whether the gesture was correctly performed.

Another technical benefit of the systems and methods of the present disclosure is changing the action set and the audio feedback based on the activity state of the user. The systems and methods disclosed herein can be used to enable the dynamic changing of action sets with respective gestures based on a determined activity state. The dynamic changing can allow for a wide-variety of inputs to be accessible to a user with limited touch sensors. For example, a user may use different inputs at work versus at home; therefore, the same gesture may be associated with different actions based on a user's location. A certain sound can be used to notify the user the work action set and associated gestures are currently active.

In some implementations, the systems and methods disclosed herein can help with solving cognitive load and textual ambiguity issues.

With reference now to the Figures, example embodiments of the present disclosure will be discussed in further detail.

FIG. 1 is an illustration of an example environment 100 in which an interactive object including a touch sensor can be implemented. Environment 100 includes a touch sensor 102 (e.g., capacitive or resistive touch sensor), or other sensor. Touch sensor 102 is shown as being integrated within various interactive objects 104. Touch sensor 102 may include one or more sensing elements such as conductive threads or other sensing lines that are configured to detect a touch input. In some examples, the conductive threads or other sensing lines are arranged to extend parallel to each other along the length of the touch sensor in a longitudinal direction. The conductive threads or other sensing lines can be laterally spaced from each other.

In some examples, a capacitive touch sensor can be formed from an interactive textile which is a textile that is configured to sense multi-touch-input. As described herein, a textile corresponds to any type of flexible woven material consisting of a network of natural or artificial fibers, often referred to as thread or yarn. Textiles may be formed by weaving, knitting, crocheting, knotting, pressing threads together or consolidating fibers or filaments together in a nonwoven manner. A capacitive touch sensor can be formed from any suitable conductive material and in other manners, such as by using flexible conductive lines including metal lines, filaments, etc. attached to a non-woven substrate.

In environment 100, interactive objects 104 include "flexible" objects, such as a shirt 104-1, a hat 104-2, a handbag 104-3 and a shoe 104-6. It is to be noted, however, that touch sensor 102 may be integrated within any type of flexible object made from fabric or a similar flexible material, such as garments or articles of clothing, garment accessories, garment containers, blankets, shower curtains, towels, sheets, bedspreads, or fabric casings of furniture, to name just a few. Examples of garment accessories may include sweat-wicking elastic bands to be worn around the head, wrist, or bicep. Other examples of garment accessories may be found in various wrist, arm, shoulder, knee, leg, and hip braces or compression sleeves. Headwear is another example of a garment accessory, e.g., sun visors, caps, and thermal balaclavas. Examples of garment containers may include waist or hip pouches, backpacks, handbags, satchels, hanging garment bags, and totes. Garment containers may be worn or carried by a user, as in the case of a backpack, or may hold their own weight, as in rolling luggage. Touch sensor 102 may be integrated within flexible objects 104 in a variety of different ways, including weaving, sewing, gluing, and so forth. Flexible objects may also be referred to as "soft" objects.

In this example, objects 104 further include "hard" objects, such as a plastic cup 104-4 and a hard smart phone casing 104-5. It is to be noted, however, that hard objects 104 may include any type of "hard" or "rigid" object made from non-flexible or semi-flexible materials, such as plastic, metal, aluminum, and so on. For example, hard objects 104 may also include plastic chairs, water bottles, plastic balls, or car parts, to name just a few. In another example, hard objects 104 may also include garment accessories such as chest plates, helmets, goggles, shin guards, and elbow guards. Alternatively, the hard or semi-flexible garment accessory may be embodied by a shoe, cleat, boot, or sandal. Touch sensor 102 may be integrated within hard objects 104 using a variety of different manufacturing processes. In one or more implementations, injection molding is used to integrate touch sensors into hard objects 104.

Touch sensor 102 enables a user to control an object 104 with which the touch sensor 102 is integrated, or to control a variety of other computing devices 106 via a network 108. Computing devices 106 are illustrated with various non-limiting example devices: server 106-1, smartphone 106-2, laptop 106-3, computing spectacles 106-4, television 106-5, camera 106-6, tablet 106-7, desktop 106-8, and smart watch 106-9, though other devices may also be used, such as home automation and control systems, sound or entertainment systems, home appliances, security systems, netbooks, and e-readers. Note that computing device 106 can be wearable (e.g., computing spectacles and smart watches), non-wearable but mobile (e.g., laptops and tablets), or relatively immobile (e.g., desktops and servers). Computing device 106 may be a local computing device, such as a computing device that can be accessed over a Bluetooth connection, near-field communication connection, or other local-network connection. Computing device 106 may be a remote computing device, such as a computing device of a cloud computing system.

Network 108 includes one or more of many types of wireless or partly wireless communication networks, such as a local-area-network (LAN), a wireless local-area-network (WLAN), a personal-area-network (PAN), a wide-area-network (WAN), an intranet, the Internet, a peer-to-peer network, point-to-point network, a mesh network, and so forth.

A touch sensor 102 can interact with computing devices 106 by transmitting touch data or other sensor data through network 108. Additionally or alternatively, the touch sensor 102 may transmit gesture data, movement data, or other data derived from sensor data generated by the touch sensor 102. Computing device 106 can use the touch data to control computing device 106 or applications at computing device 106. As an example, consider that the touch sensor 102 integrated at shirt 104-1 may be configured to control the user's smartphone 106-2 in the user's pocket, television 106-5 in the user's home, smart watch 106-9 on the user's wrist, or various other appliances in the user's house, such as thermostats, lights, music, and so forth. For example, the user may be able to swipe up or down on touch sensor 102 integrated within the user's shirt 104-1 to cause the volume on television 106-5 to go up or down, to cause the temperature controlled by a thermostat in the user's house to increase or decrease, or to turn on and off lights in the user's house. Note that any type of touch, tap, swipe, hold, or stroke gesture may be recognized by touch sensor 102.

Figure 2:
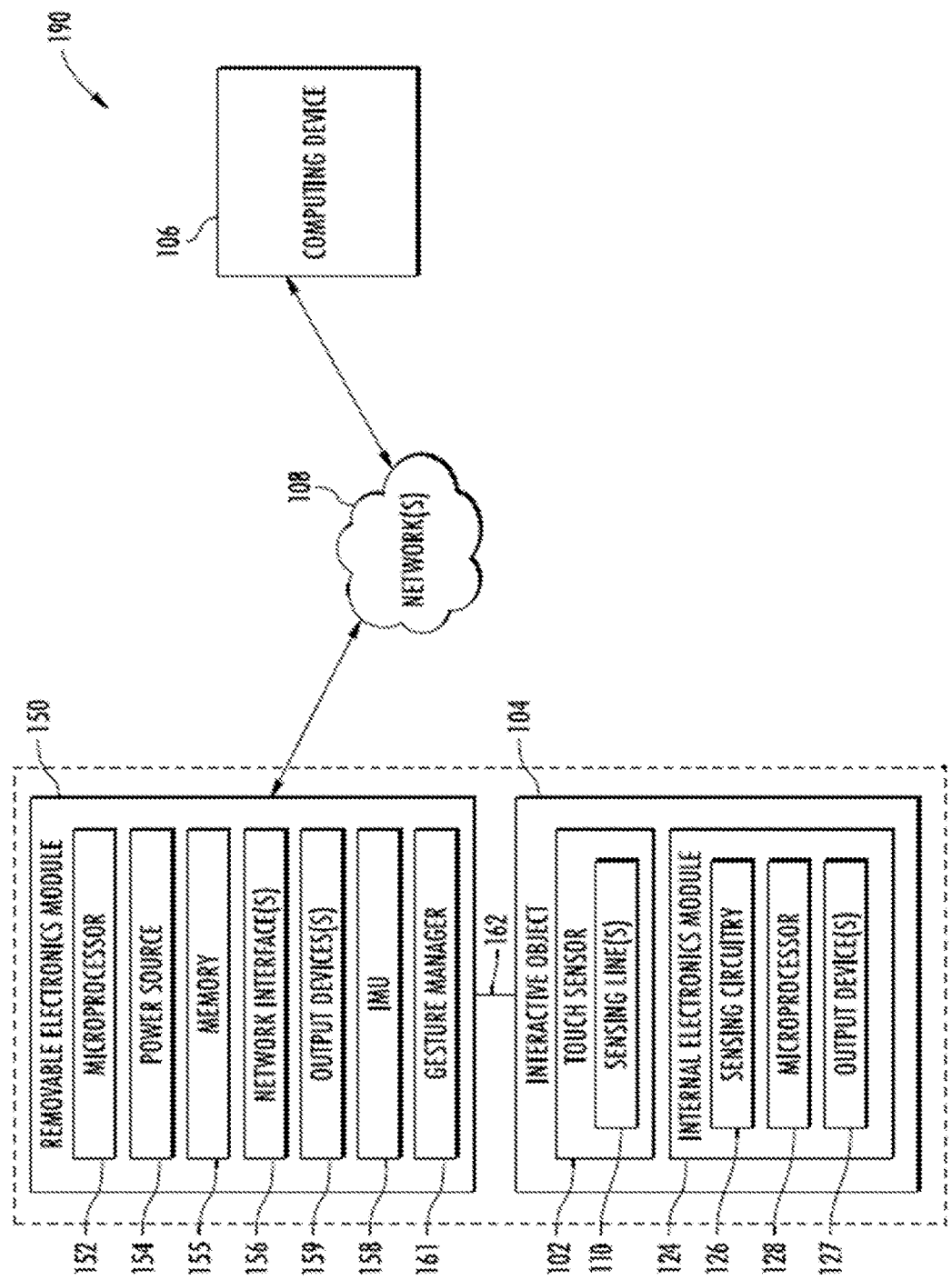
FIG. 2 is a block diagram of an example computing environment that includes an interactive object having a touch sensor in accordance with example embodiments of the present disclosure.

In more detail, consider FIG. 2 which illustrates an example system 190 that includes an interactive object 104, a removable electronics module 150, and a computing device 106. In system 190, touch sensor 102 is integrated in an object 104, which may be implemented as a flexible object (e.g., shirt 104-1, hat 104-2, or handbag 104-3) or a hard object (e.g., plastic cup 104-4 or smart phone casing 104-5).

Touch sensor 102 is configured to sense touch-input from a user when one or more fingers of the user's hand touch or approach touch sensor 102. Touch sensor 102 may be configured as a capacitive touch sensor or resistive touch sensor to sense single-touch, multi-touch, and/or full-hand touch-input from a user. To enable the detection of touch-input, touch sensor 102 includes sensing lines 110. Sensing elements may include various shapes and geometries. In some examples, sensing lines 110 can be formed as a grid, array, or parallel pattern of sensing lines so as to detect touch input. In some implementations, the sensing lines 110 do not alter the flexibility of touch sensor 102, which enables touch sensor 102 to be easily integrated within interactive objects 104.

Interactive object 104 includes an internal electronics module 124 (also referred to as internal electronics device) that is embedded within interactive object 104 and is directly coupled to sensing lines 110. Internal electronics module 124 can be communicatively coupled to a removable electronics module 150 (also referred to as a removable electronics device) via a communication interface 162. Internal electronics module 124 contains a first subset of electronic circuits or components for the interactive object 104, and removable electronics module 150 contains a second, different, subset of electronic circuits or components for the interactive object 104. As described herein, the internal electronics module 124 may be physically and permanently embedded within interactive object 104, whereas the removable electronics module 150 may be removably coupled to interactive object 104.

In system 190, the electronic components contained within the internal electronics module 124 include sensing circuitry 126 that is coupled to sensing lines 110 that form the touch sensor 102. In some examples, the internal electronics module includes a flexible printed circuit board (PCB). The printed circuit board can include a set of contact pads for attaching to the conductive lines. In some examples, the printed circuit board includes a microprocessor. For example, wires from conductive threads may be connected to sensing circuitry 126 using flexible PCB, creping, gluing with conductive glue, soldering, and so forth. In one embodiment, the sensing circuitry 126 can be configured to detect a user-inputted touch-input on the conductive threads that is pre-programmed to indicate a certain request. In one embodiment, when the conductive threads form a tunneled pattern as described herein, sensing circuitry 126 can be configured to also detect the location of the touch-input on sensing line 110, as well as motion of the touch-input. For example, when an object, such as a user's finger, touches sensing lines 110, the position of the touch can be determined by sensing circuitry 126 by detecting a change in capacitance on the sensing lines 110. The touch-input may then be used to generate touch data usable to control a computing device 106. For example, the touch-input can be used to determine various gestures, such as single-finger touches (e.g., touches, taps, and holds), multi-finger touches (e.g., two-finger touches, two-finger taps, two-finger holds, and pinches), single-finger and multi-finger swipes (e.g., swipe up, swipe down, swipe left, swipe right), and full-hand interactions (e.g., touching the textile with a user's entire hand, covering textile with the user's entire hand, pressing the textile with the user's entire hand, palm touches, and rolling, twisting, or rotating the user's hand while touching the textile).

Internal electronics module 124 can include various types of electronics, such as sensing circuitry 126, sensors (e.g., capacitive touch sensors woven into the garment, microphones, or accelerometers), output devices (e.g., LEDs, speakers, or micro-displays), electrical circuitry, and so forth. Removable electronics module 150 can include various electronics that are configured to connect and/or interface with the electronics of internal electronics module 124. Generally, the electronics contained within removable electronics module 150 are different than those contained within internal electronics module 124, and may include electronics such as microprocessor 152, power source 154 (e.g., a battery), memory 155, network interface 156 (e.g., Bluetooth, WiFi, USB), sensors (e.g., accelerometers, heart rate monitors, pedometers, IMUs), output devices (e.g., speakers, LEDs), and so forth.

In some examples, removable electronics module 150 is implemented as a strap or tag that contains the various electronics. The strap or tag, for example, can be formed from a material such as rubber, nylon, plastic, metal, or any other type of fabric. Notably, however, removable electronics module 150 may take any type of form. For example, rather than being a strap, removable electronics module 150 could resemble a circular or square piece of material (e.g., rubber or nylon).

The inertial measurement unit(s) (IMU(s)) 158 can generate sensor data indicative of a position, velocity, and/or an acceleration of the interactive object. The IMU(s) 158 may generate one or more outputs describing one or more three-dimensional motions of the interactive object 104. The IMU(s) may be secured to the internal electronics module 124, for example, with zero degrees of freedom, either removably or irremovably, such that the inertial measurement unit translates and is reoriented as the interactive object 104 is translated and is reoriented. In some embodiments, the inertial measurement unit(s) 158 may include a gyroscope or an accelerometer (e.g., a combination of a gyroscope and an accelerometer), such as a three-axis gyroscope or accelerometer configured to sense rotation and acceleration along and about three, generally orthogonal axes. In some embodiments, the inertial measurement unit(s) may include a sensor configured to detect changes in velocity or changes in rotational velocity of the interactive object and an integrator configured to integrate signals from the sensor such that a net movement may be calculated, for instance by a processor of the inertial measurement unit, based on an integrated movement about or along each of a plurality of axes.

Communication interface 162 enables the transfer of power and data (e.g., the touch-input detected by sensing circuitry 126) between the internal electronics module 124 and the removable electronics module 260. In some implementations, communication interface 162 may be implemented as a connector that includes a connector plug and a connector receptacle. The connector plug may be implemented at the removable electronics module 150 and is configured to connect to the connector receptacle, which may be implemented at the interactive object 104. One or more communication interface(s) may be included in some examples. For instance, a first communication interface may physically couple the removable electronics module 150 to one or more computing devices 106, and a second communication interface may physically couple the removable electronics module 150 to interactive object 104.

In system 190, the removable electronics module 150 includes a microprocessor 152, a power source 154, memory 155, one or more output devices 159, an IMU 158, a gesture manager 161, and network interface 156. Power source 154 may be coupled, via communication interface 162, to sensing circuitry 126 to provide power to sensing circuitry 126 to enable the detection of touch-input and may be implemented as a small battery. When touch-input is detected by sensing circuitry 126 of the internal electronics module 124, data representative of the touch-input may be communicated, via communication interface 162, to microprocessor 152 of the removable electronics module 150. Microprocessor 152 may then analyze the touch-input data to generate one or more control signals, which may then be communicated to a computing device 106 (e.g., a smart phone, server, cloud computing infrastructure, etc.) via the network interface 156 to cause the computing device to initiate a particular functionality. Generally, network interfaces 156 are configured to communicate data, such as touch data, over wired, wireless, or optical networks to computing devices. By way of example and not limitation, network interfaces 156 may communicate data over a local-area-network (LAN), a wireless local-area-network (WLAN), a personal-area-network (PAN) (e.g., Bluetooth™), a wide-area-network (WAN), an intranet, the Internet, a peer-to-peer network, point-to-point network, a mesh network, and the like (e.g., through network 108 of FIG. 1 and FIG. 2).

Object 104 may also include one or more output devices 127 configured to provide a haptic response, a tactical response, an audio response, a visual response, or some combination thereof. Similarly, removable electronics module 150 may include one or more output devices 159 configured to provide a haptic response, tactical response, and audio response, a visual response, or some combination thereof. Output devices 127 may include visual output devices, such as one or more light-emitting diodes (LEDs), audio output devices such as one or more speakers, one or more tactile output devices, and/or one or more haptic output devices. In some examples, the one or more output devices 159 are formed as part of removable electronics module 150, although this is not required.

In one example, an output device 127 can include one or more LEDs configured to provide different types of output signals. For example, the one or more LEDs can be configured to generate a circular pattern of light, such as by controlling the order and/or timing of individual LED activations. Other lights and techniques may be used to generate visual patterns including circular patterns. In some examples, one or more LEDs may produce different colored light to provide different types of visual indications. Output devices 127 may include a haptic or tactile output device that provides different types of output signals in the form of different vibrations and/or vibration patterns. In yet another example, output devices 127 may include a haptic output device such as may tighten or loosen an interactive garment with respect to a user. For example, a clamp, clasp, cuff, pleat, pleat actuator, band (e.g., contraction band), or other device may be used to adjust the fit of a garment on a user (e.g., tighten and/or loosen). In some examples, an interactive textile may be configured to tighten a garment such as by actuating conductive threads within the touch sensor 102.

A gesture manager 161 can be capable of interacting with applications at computing devices 106 and touch sensor 102 effective to aid, in some cases, control of applications through touch-input received by touch sensor 102. For example, gesture manager 161 can interact with applications. In FIG. 2, gesture manager 161 is illustrated as implemented at removable electronics module 150. It will be appreciated, however, that gesture manager 161 may be implemented at internal electronics module 124, a computing device 106 remote from the interactive object, or some combination thereof. A gesture manager 161 may be implemented as a standalone application in some embodiments. In other embodiments, a gesture manager 161 may be incorporated with one or more applications at a computing device.

A gesture or other predetermined motion can be determined based on touch data detected by the touch sensor 102 and/or an inertial measurement unit 158 or other sensor. For example, gesture manager 161 can determine a gesture based on touch data, such as single-finger touch gesture, a double-tap gesture, a two-finger touch gesture, a swipe gesture, and so forth. As another example, gesture manager 161 can determine a gesture based on movement data such as a velocity, acceleration, etc. as can be determined by inertial measurement unit 158.

A functionality associated with a gesture can be determined by gesture manager 161 and/or an application at a computing device 106. In some examples, it is determined whether the touch data corresponds to a request to perform a particular functionality. For example, the gesture manager 161 can determine whether touch data corresponds to a user input or gesture that is mapped to a particular functionality, such as initiating a vehicle service, triggering a text message or other notification, answering a phone call, creating a journal entry, and so forth. As described throughout, any type of user input or gesture may be used to trigger the functionality, such as swiping, tapping, or holding touch sensor 102. In one or more implementations, a gesture manager 161 can enable application developers or users to configure the types of user input or gestures that can be used to trigger various different types of functionalities. For example, a gesture manager 161 can cause a particular functionality to be performed, such as by sending a text message or other communication, answering a phone call, creating a journal entry, increase the volume on a television, turn on lights in the user's house, open the automatic garage door of the user's house, and so forth.

While internal electronics module 124 and removable electronics module 150 are illustrated and described as including specific electronic components, it is to be appreciated that these modules may be configured in a variety of different ways. For example, in some cases, electronic components described as being contained within internal electronics module 124 may be at least partially implemented at the removable electronics module 150, and vice versa. Furthermore, internal electronics module 124 and removable electronics module 150 may include electronic components other than those illustrated in FIG. 2, such as sensors, light sources (e.g., LED's), displays, speakers, and so forth.

Figure 3:
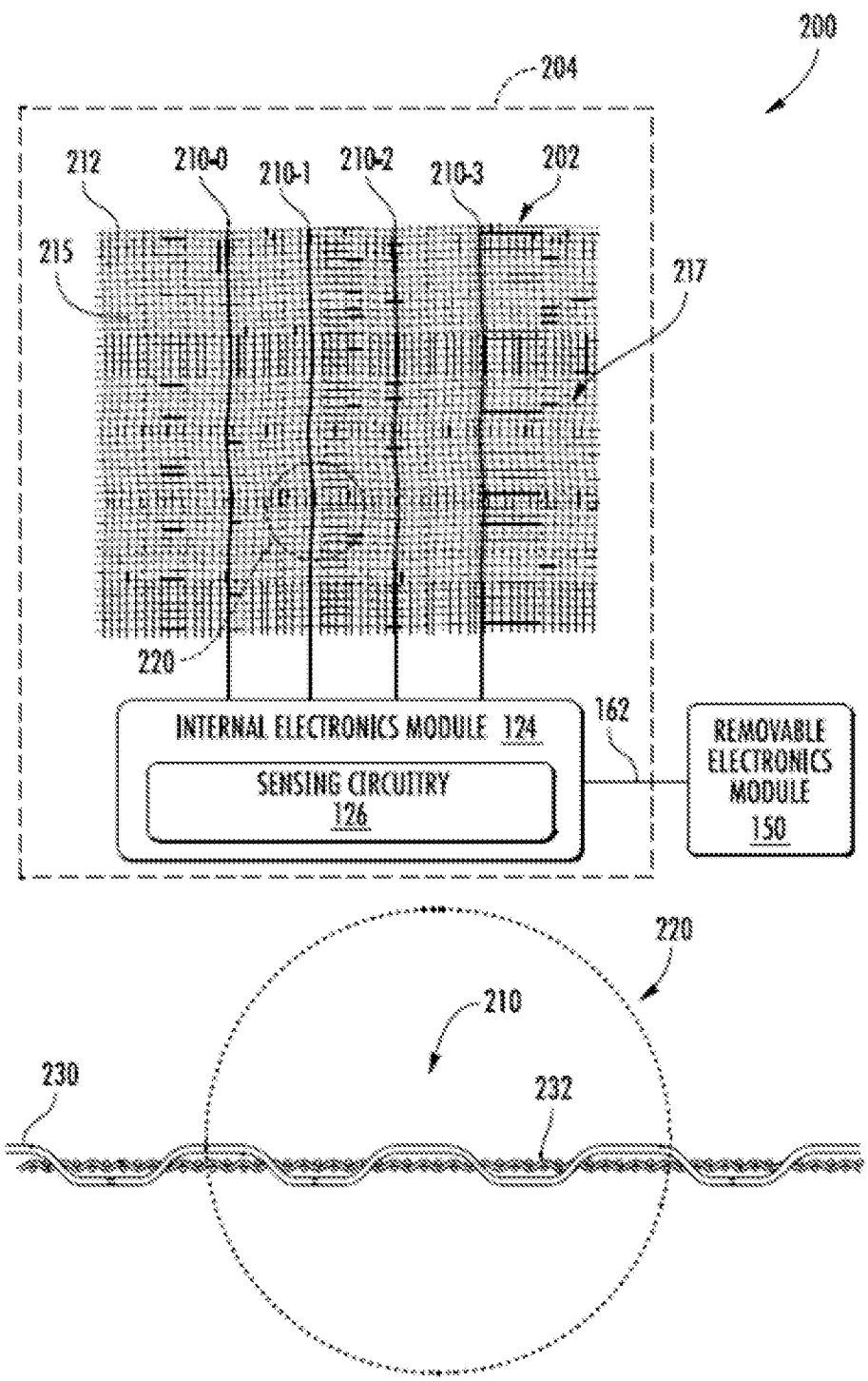
FIG. 3 illustrates an example of a sensor system, such as can be integrated with an interactive object in accordance with example embodiments of the present disclosure.

FIG. 3 illustrates an example of a sensor system 200, such as can be integrated with an interactive object 204 in accordance with one or more implementations. In this example, the sensing elements (e.g., sensing lines 110 in FIG. 2) are implemented as conductive threads 210 on or within a substrate 215. Touch sensor 202 includes non-conductive threads 212 woven with conductive threads 210 to form a capacitive touch sensor 202 (e.g., interactive textile). It is noted that a similar arrangement may be used to form a resistive touch sensor. Non-conductive threads 212 may correspond to any type of non-conductive thread, fiber, or fabric, such as cotton, wool, silk, nylon, polyester, and so forth.

At 220, a zoomed-in view of conductive thread 210 is illustrated. Conductive thread 210 includes a conductive wire 230 or a plurality of conductive filaments that are twisted, braided, or wrapped with a flexible thread 232. As shown, the conductive thread 210 can be woven with or otherwise integrated with the non-conductive threads 212 to form a fabric or a textile. Although a conductive thread and textile is illustrated, it will be appreciated that other types of sensing elements and substrates may be used, such as flexible metal lines formed on a plastic substrate.

In one or more implementations, conductive wire 230 is a thin copper wire. It is to be noted, however, that the conductive wire 230 may also be implemented using other materials, such as silver, gold, or other materials coated with a conductive polymer. The conductive wire 230 may include an outer cover layer formed by braiding together non-conductive threads. The flexible thread 232 may be implemented as any type of flexible thread or fiber, such as cotton, wool, silk, nylon, polyester, and so forth.

Capacitive touch sensor 202 can be formed cost-effectively and efficiently, using any conventional weaving process (e.g., jacquard weaving or 3D-weaving), which involves interlacing a set of longer threads (called the warp) with a set of crossing threads (called the weft). Weaving may be implemented on a frame or machine known as a loom, of which there are a number of types. Thus, a loom can weave non-conductive threads 212 with conductive threads 210 to create a capacitive touch sensor 202. In another example, capacitive touch sensor 202 can be formed using a predefined arrangement of sensing lines formed from a conductive fabric such as an electro-magnetic fabric including one or more metal layers.

The conductive threads 210 can be formed into the touch sensor 202 in any suitable pattern or array. In one embodiment, for instance, the conductive threads 210 may form a single series of parallel threads. For instance, in one embodiment, the capacitive touch sensor may comprise a single plurality of parallel conductive threads conveniently located on the interactive object, such as on the sleeve of a jacket.

In example system 200, sensing circuitry 126 is shown as being integrated within object 104, and is directly connected to conductive threads 210. During operation, sensing circuitry 126 can determine positions of touch-input on the conductive threads 210 using self-capacitance sensing or mutual capacitive sensing.

For example, when configured as a self-capacitance sensor, sensing circuitry 126 charges can charge a selected conductive thread 210 by applying a control signal (e.g., a sine signal) to the selected conductive thread 210. The control signal may be referred to as a scanning voltage in some examples and the processing of determining the capacitance of a selected conductive thread may be referred to as scanning. In some examples, the control signal can be applied to a selected conductive thread while grounding or applying a low-level voltage to the other conductive threads. When an object, such as the user's finger, touches the sensor of conductive thread 210, the capacitive coupling between the conductive thread 210 that is being scanned and system ground may be increased, which changes the capacitance sensed by the touched conductive thread 210. This process can be repeated by applying the scanning voltage to each selected conductive thread while grounding the remaining non-selected conductive threads. In some examples, the conductive threads can be scanned individually, proceeding through the set of conductive threads in sequence. In other examples, more than one conductive thread may be scanned simultaneously.

Sensing circuitry 126 uses the change in capacitance to identify the presence of the object (e.g., user's finger, stylus, etc.). When an object, such as the user's finger, touches the sensor of conductive threads, the capacitance changes on the conductive threads (e.g., increases or decreases). Sensing circuitry 126 uses the change in capacitance on conductive threads to identify the presence of the object. To do so, sensing circuitry 126 detects a position of the touch-input by scanning the conductive threads to detect changes in capacitance. Sensing circuitry 126 determines the position of the touch-input based on conductive threads having a changed capacitance. Other sensing techniques such as mutual capacitive sensing may be used in example embodiments.

The conductive thread 210 and sensing circuitry 126 is configured to communicate the touch data that is representative of the detected touch-input to gesture manager 161 (e.g., at removable electronics module 150 in FIG. 2). The microprocessor 152 may then cause communication of the touch data, via network interface 156, to computing device 106 to enable the device to determine gestures based on the touch data, which can be used to control object 104, computing device 106, or applications implemented at computing device 106. In some implementations, a predefined motion may be determined by the internal electronics module and/or the removable electronics module and data indicative of the predefined motion can be communicated to a computing device 106 to control object 104, computing device 106, or applications implemented at computing device 106.

In accordance with some embodiments, a plurality of sensing lines can be formed from a multilayered flexible film to facilitate a flexible sensing line. For example, the multilayered film may include one or more flexible base layers such as a flexible textile, plastic, or other flexible material. One or more metal layers may extend over the flexible base layer(s). Optionally, one or more passivation layers can extend over the one or more flexible base layers and the one or more metal layer(s) to promote adhesion between the metal layer(s) and the base layer(s). In accordance with some examples, a multilayered sheet including one or more flexible base layers, one or more metal layers, and optionally one or more passivation layers can be formed and then cut, etched, or otherwise divided into individual sensing lines. Each sensing line can include a line of the one or more metal layers formed over a line of the one or more flexible base layers. Optionally, a sensing line can include a line of one or more passivation layers overlying the one or more flexible base layers. An electromagnetic field shielding fabric can be used to form the sensing lines in some examples.

The plurality of conductive threads 210 forming touch sensor 202 are integrated with non-conductive threads 212 to form flexible substrate 215 having a first surface 217. opposite a second side (or surface) in a direction orthogonal to the first side and the second side. Any number of conductive threads may be used to form a touch sensor. Moreover, any number of conductive threads may be used to form the plurality of first conductive threads and the plurality of second conductive threads. Additionally, the flexible substrate may be formed from one or more layers. For instance, the conductive threads may be woven with multiple layers of non-conductive threads. In this example, the conductive threads are formed on the first surface only. In other examples, a first set of conductive threads can be formed on the first surface and a second set of conductive threads at least partially formed on the second surface.

One or more control circuits of the sensor system 200 can obtain touch data associated with a touch input to touch sensor 202. The one or more control circuits can include sensing circuitry 126 and/or a computing device such as a microprocessor 128 at the internal electronics module, microprocessor 152 at the removable electronics module 150, and/or a remote computing device 106. The one or more control circuits can implement gesture manager 161 in example embodiments. The touch data can include data associated with a respective response by each of the plurality of conductive threads 210. The touch data can include, for example, a capacitance associated with conductive threads 210-1, 210-2, 210-3, and 210-4. In some examples, the control circuit(s) can determine whether the touch input is associated with a first subset of conductive threads exposed on the first surface or a second subset of conductive threads exposed on the second surface. The control circuit(s) can classify the touch input as associated with a particular subset based at least in part on the respective response to the touch input by the plurality of conductive sensing elements.

The control circuits(s) can be configured to detect a surface of the touch sensor at which a touch input is received, detect one or more gestures or other user movements in response to touch data associated with a touch input, and/or initiate one or more actions in response to detecting the gesture or other user movement. By way of example, control circuit(s) can obtain touch data that is generated in response to a touch input to touch sensor 202. The touch data can be based at least in part on a response (e.g., resistance or capacitance) associated with sensing elements from each subset of sensing elements. The control circuit(s) can determine whether the touch input is associated with a first surface of the touch sensor or a second surface of the touch sensor based at least in part on the response associated with the first sensing element and the response associated with the second sensing element. The control circuit(s) can selectively determine whether a touch input corresponds to a particular input gesture based at least in part on whether the touch input is determined to have been received at first surface of the touch sensor or a second surface of the touch sensor. Notably, the control circuit(s) can analyze the touch data from each subset of sensing elements to determine whether a particular gesture has been performed. In this regard, the control circuits can utilize the individual subsets of elements to identify the particular surface of the touch sensor. However, the control circuits can utilize the full set of sensing elements to identify whether a gesture has been performed.

Figure 4:
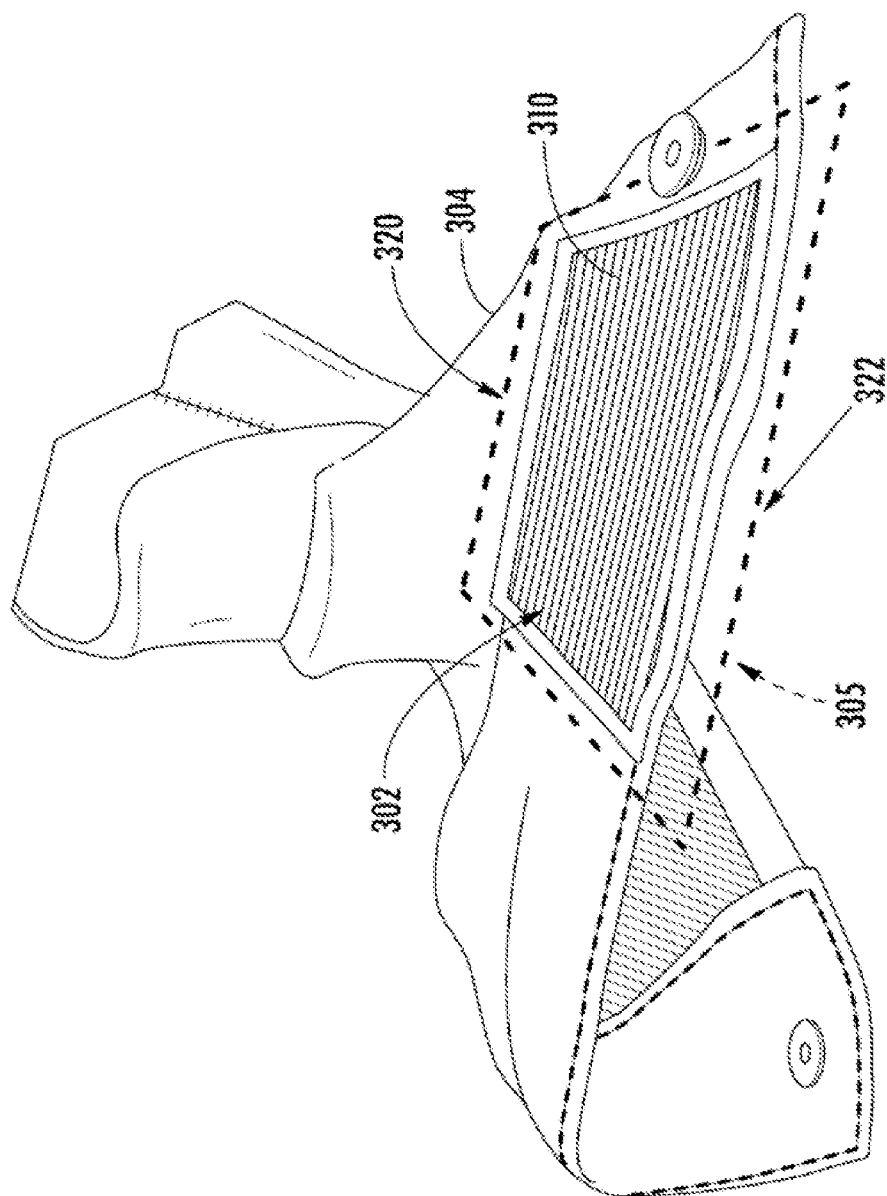
FIG. 4 depicts an example of a touch sensor integrated with an interactive object in accordance with example embodiments of the present disclosure.

FIG. 4 is a perspective view of an example of an interactive object including a capacitive touch sensor 302 in accordance with example embodiments of the present disclosure. In this example, the interactive object is an interactive garment 304 having a capacitive touch sensor 302 integrated in the cuff of a sleeve. By way of example, the user can perform a gesture by brushing in on the cuff of the interactive object 104 cuff where the capacitive touch sensor 302 is placed. Gesture manager 161 can be configured to initiate and/or implement one or more functionalities in response to the brush in gesture. For example, a user may perform a brush in gesture in order to receive a notification related to an application at the remote computing device (e.g., having a text message converted into an audible output at the remote computing device). Note that any type of touch, tap, swipe, hold, or stroke gesture may be recognized by capacitive touch sensor 302. In an alternate example, a resistive touch sensor may be used rather than a capacitive touch sensor.

The conductive sensing elements 310 in FIG. 4 are positioned at a touch sensor area 305. The sensing elements 310 can be partitioned into subsets of sensing elements to enable a sensor system to distinguish between touch inputs at an intended touch input surface 320 and touch inputs at an unintended second surface 322. The second surface can be positioned toward a user's body when the interactive garment is worn. In traditional designs, it may be difficult to distinguish a touch between the intended touch input surface 320 and the unintended second surface 322. Typically, thick padding is provided between the user's body and the touch sensor to attenuate the capacitive signal generated in response to the user's body at the unintended second surface 322.

In accordance with example embodiments, the first subset of conductive sensing elements can be coupled to a first side of a flexible substrate and the second subset of conductive sensing elements can be coupled to a second side of the flexible substrate. The first side can be positioned closer to the intended touch input surface 320 and the second side can be positioned further from the intended touch input surface 320 and closer to the second surface 322 which will be adjacent to the user when worn. For example, the first side can be adjacent to the intended touch input surface and the second side can be adjacent to one or more portions of the user's body when the interactive garment is worn by the user. In some embodiments, the first side of the flexible substrate and the second side of the flexible substrate can be separated in the direction orthogonal to the first side and the second side of the flexible substrate. By positioning subsets of sensing elements on opposite sides of the substrate, the capacitive signal generated by the user's body at the second surface can be distinguished from the capacitive signal generated by the touch input at the intended touch input surface.

In accordance with example embodiments, the first and second subsets of sensing elements can be separated in a vertical direction to provide signal differentiation to distinguish inputs provided at the intended input surface from inputs provided at the unintended second surface. For example, the sensing elements can be arranged as parallel sensing lines as shown in FIG. 4. The sensing lines can be elongated in a first direction with a separation therebetween in a second direction orthogonal to the first direction. A first subset of the parallel sensing lines and a second subset of the parallel sensing lines can be separated in a direction orthogonal to the first direction and the second direction. Notably, this separation can be provided with or without the use of a flexible substrate to which the lines are coupled. A touch input provided at the intended touch input surface (e.g., +vertical axis 205) can generate a stronger signal (e.g., capacitance) on the first subset of lines than the second subset of lines. A touch input provided at the unintended second surface (e.g., −vertical axis) can generate a stronger signal (e.g., capacitance) on the second subset of lines than the first subset of lines.

Figure 5:
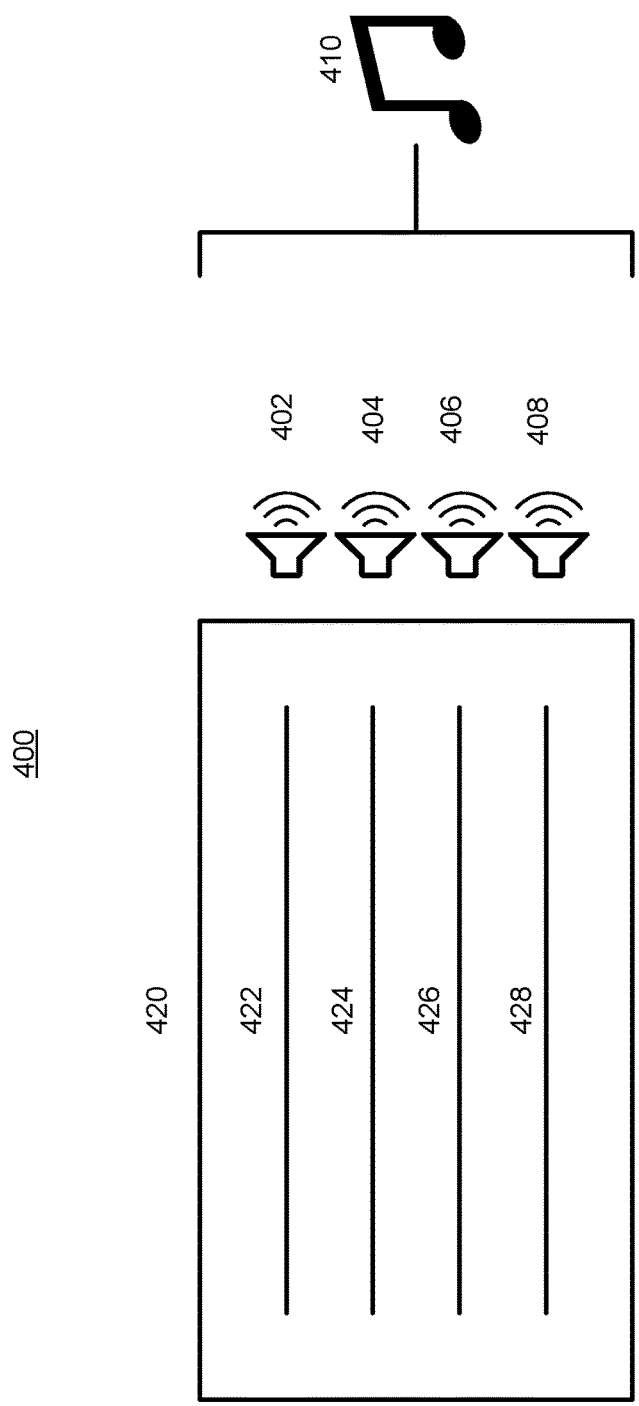
FIG. 5 depicts a block diagram of an example line-specific audio feedback system according to example embodiments of the present disclosure.

FIG. 5 depicts an example sensing line system 400 in which each sensing line is associated with a respective line-specific audio feedback. The sensing lines 420 can be a plurality of sensing lines 420 attached to a touch sensor or may be separately attached to a plurality of touch sensors. The sensing line system 400 can further include gesture validity determination which can cause a gesture validity audio feedback 410 to be determined and provided.

The sensing line system 400 depicted in FIG. 5 can be utilized for training a user to correctly complete gestures. For example, the sensing lines 420 can be implemented into a smart wearable with one or more touch sensors, and one or more processors in a jacket, backpack, etc. The first sensing line 422 can be associated with a first sound 402, the second sensing line 424 can be associated with a second sound 404, the third sensing line 426 can be associated with a third sound 406, and the fourth sensing line 428 can be associated with a fourth sound 408. Therefore, when a user contacts a second sensing line 424, a second sound 404 can be provided in real-time. The user can then hear real-time feedback of which of the sensing lines 420 are being contacted.

At the completion of the gesture, a gesture validity can be determined, which can cause a gesture validity audio feedback 410 to be determined and provided. The line-specific audio feedback paired with the gesture validity audio feedback 410 can allow for user gesture training with an intuitive interface for inputs.

In some implementations the line-specific audio feedbacks can include sounds with a common musical key but different respective notes. For example, the first sound 402, the second sound 404, the third sound 406, and the fourth sound 408 can all share a common musical key, but the first sound 402 can be differentiated from the other sounds based on the musical note. Moreover, in some implementations, the gesture validity audio feedback 410 can be an on-key sound if the gesture is valid or an off-key sound if the gesture is invalid. Additionally and/or alternatively, the gesture validity audio feedback 410 can include the note of at least one of the selected sensing lines 420 in response to the gesture being valid. In some implementations, the gesture validity audio feedback 410 can include a playback of each of the respective line-specific audio feedbacks of the associated sensing lines in the gesture if the gesture is determined to be valid.

Figure 6:
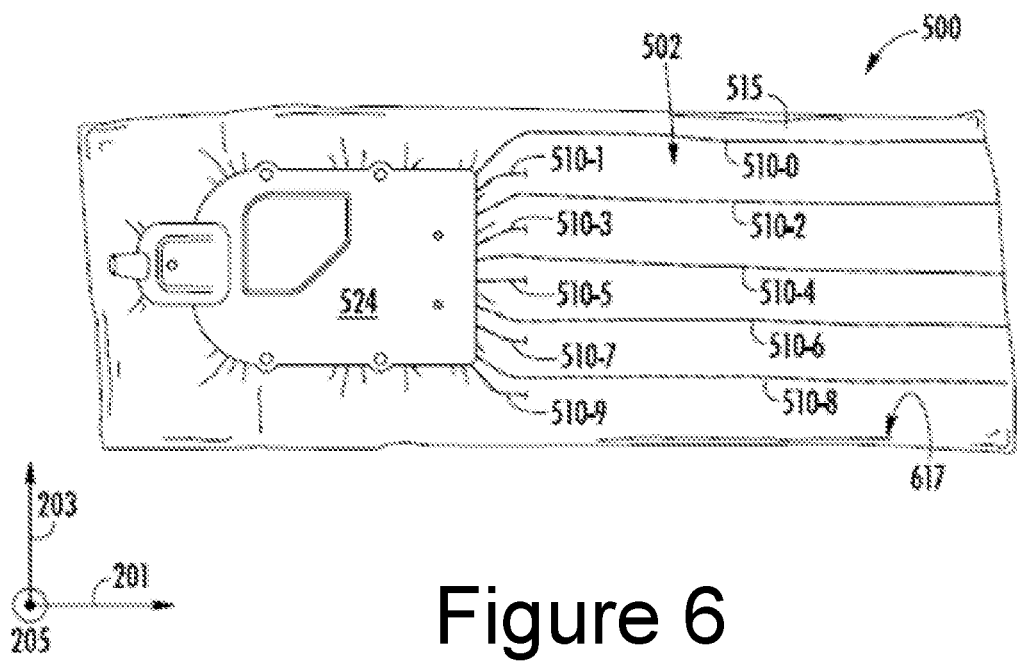
FIGS. 6 and 7 are top and bottom views, respectively, depicting an example of a touch sensor including individual subsets of sensing lines coupled to opposite sides of a flexible substrate in accordance with example embodiments of the present disclosure.
Figure 7:
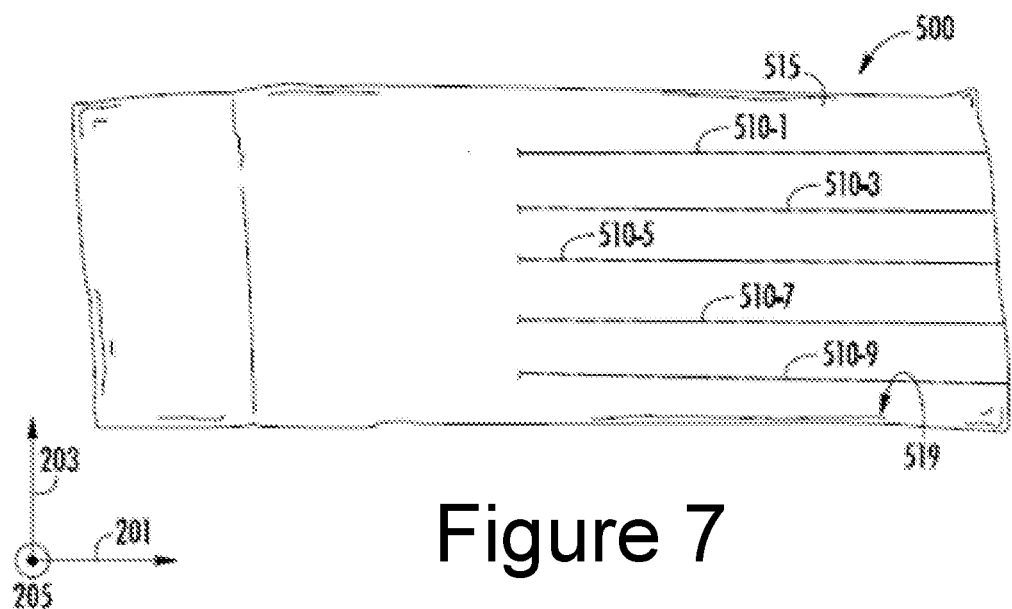

FIG. 6 and FIG. 7 are top and bottom views, respectively, depicting an example of a touch sensor including individual subsets of sensing lines coupled to opposite sides of a flexible substrate in accordance with example embodiments of the present disclosure. A sensor assembly 500 includes a touch sensor 502 and an internal electronics module 524. Internal electronics module 524 is one example of an internal electronics module 124 as depicted in FIG. 2. Touch sensor 502 is one example of a touch sensor 102 as illustrated in FIGS. 1 and 2, and can be configured as a capacitive touch sensor or resistive touch sensor in example embodiments.

Touch sensor 502 is formed from a plurality of conductive threads 510-0 to 510-9. Conductive threads 510-0 to 510-9 are one example of sensing elements 110. Conductive threads 510-0 to 510-9 are an example of parallel sensing lines coupled to a substrate and extending in a longitudinal direction to receive touch input. Internal electronics module 524 may include sensing circuitry (not shown) in electrical communication with the plurality of conductive threads 510-0 to 510-9. Internal electronics module 524 may include one or more communication ports that can couple to a communications cable to provide communication with a removable electronics module. A communication port can additionally or alternatively be coupled to a communication cable to provide communication with various input and/or output devices. Output devices may include an audible output device such as a speaker, a visual output device such as a light (e.g., LED), or a haptic output device such as a haptic motor. Any suitable type of output device may be provided as an output device.

The set of conductive threads 510 can be woven or otherwise integrated with a plurality of non-conductive threads to form an interactive textile substrate 515. More particularly, the conductive threads 510 can be formed on opposite sides of substrate 515. A first subset of conductive threads 510-0, 510-2, 510-4, 510-6, and 510-8 can be woven with or otherwise coupled to the first side 517 of the interactive textile and the second subset of conductive threads 510-1, 510-3, 510-5, 510-7, and 510-9 can be woven with or otherwise coupled to the second side 519 of the interactive textile. The first subset of conductive threads can be formed on the first side 517 adjacent to a first surface of the touch sensor and the second subset of conductive threads can be formed on the opposite side 519 adjacent to a second surface of the touch sensor. A touch input to the touch sensor can be detected by the plurality of conductive threads using sensing circuitry of internal electronics module 524 connected to the one or more conductive threads. The sensing circuitry can generate touch data (e.g., raw sensor data or data derived from the raw sensor data) based on the touch input. The sensing circuitry and/or other control circuitry (e.g., a local or remote processor) can analyze the touch data to determine a surface of the touch sensor associated with the touch input. In some examples, the control circuitry can ignore touch inputs associated with the second surface, while analyzing touch inputs associated with the first surface to detect one or more predetermined gestures. As another example, the control circuitry can analyze touch inputs associated with the first surface for a first set of predetermined gestures and can analyze touch inputs associated with the second surface for a second set of predetermined gestures.

With reference to FIG. 6, the first side 517 of flexible substrate 515 can correspond to an intended touch input surface for the touch sensor when integrated with an interactive object. For example, sensor assembly 500 can be integrated with an object to form an interactive object having a touch input surface adjacent to the first side 517 of substrate 515. The second side 519 depicted in FIG. 7 can be adjacent to a user's body when an interactive garment incorporating the sensor assembly is worn by the user.

Conductive threads 510-0 to 510-9 can be formed on or within the textile-based substrate 515. By way of example, textile-based substrate 515 may be formed by weaving, embroidering, stitching, or otherwise integrating conductive threads 510-0 to 510-9 with a set of nonconductive threads.

The conductive threads are coupled to a connecting ribbon 514 in some examples, which can be utilized to position the conductive lines for connection to a plurality of electrical contact pads (not shown) of internal electronics module 524. The plurality of conductive threads 510-0 to 510-9 can be collected and organized using a ribbon with a pitch that matches a corresponding pitch of connection points of an electronic component such as a component of internal electronics module 524. It is noted, however, that a connecting ribbon is not required.

The first subset of conductive threads 510-0, 510-2, 510-4, 510-6, and 510-8 extend from the connecting ribbon 514 in the direction of longitudinal axis 201 with a spacing therebetween in the lateral direction. More particularly, the first subset of conductive threads is coupled to the first side 517 of flexible substrate 515. The first subset of conductive threads can be coupled to the first side of the flexible substrate using any suitable technique. For example, flexible substrate 515 can be formed by weaving nonconductive threads with conductive threads 510. In another example, the first subset of conductive threads 510 can be embroidered to the first side of flexible substrate 515. Other techniques such as gluing, heat pressing, or other fastening techniques may be used.

The second subset of conductive threads 510-1, 510-3, 510-5, 510-7, and 510-9 extend from the connecting ribbon 514 on the first side 517 of the flexible substrate for a limited distance. The second subset of conductive threads extend through the flexible substrate such that they are at least partially exposed on the second side 519 of the flexible substrate. In some examples, the portion of the second subset of conductive threads at the first side can be loose or otherwise not coupled to the flexible substrate 515. In other examples the second subset of conductive threads can be attached to the first side of flexible substrate 515 before passing through the flexible substrate to the second side 519. At the second side 519, conductive threads 510-1, 510-3, 510-5, 510-7, and 510-9 extend in the longitudinal direction. The second subset of conductive threads can be coupled to the second side of the flexible substrate using any suitable technique such as those earlier described with the first subset of conductive threads.

A similar pre-fabricated sensor assembly may additionally or alternatively include other types of sensors. For example, a capacitive touch sensor utilizing a thin film of conductive materials may be utilized in place of conductive thread. In some examples, resistive touch sensors can be formed in a similar manner to capacitive touch sensors as described.

Figure 8:
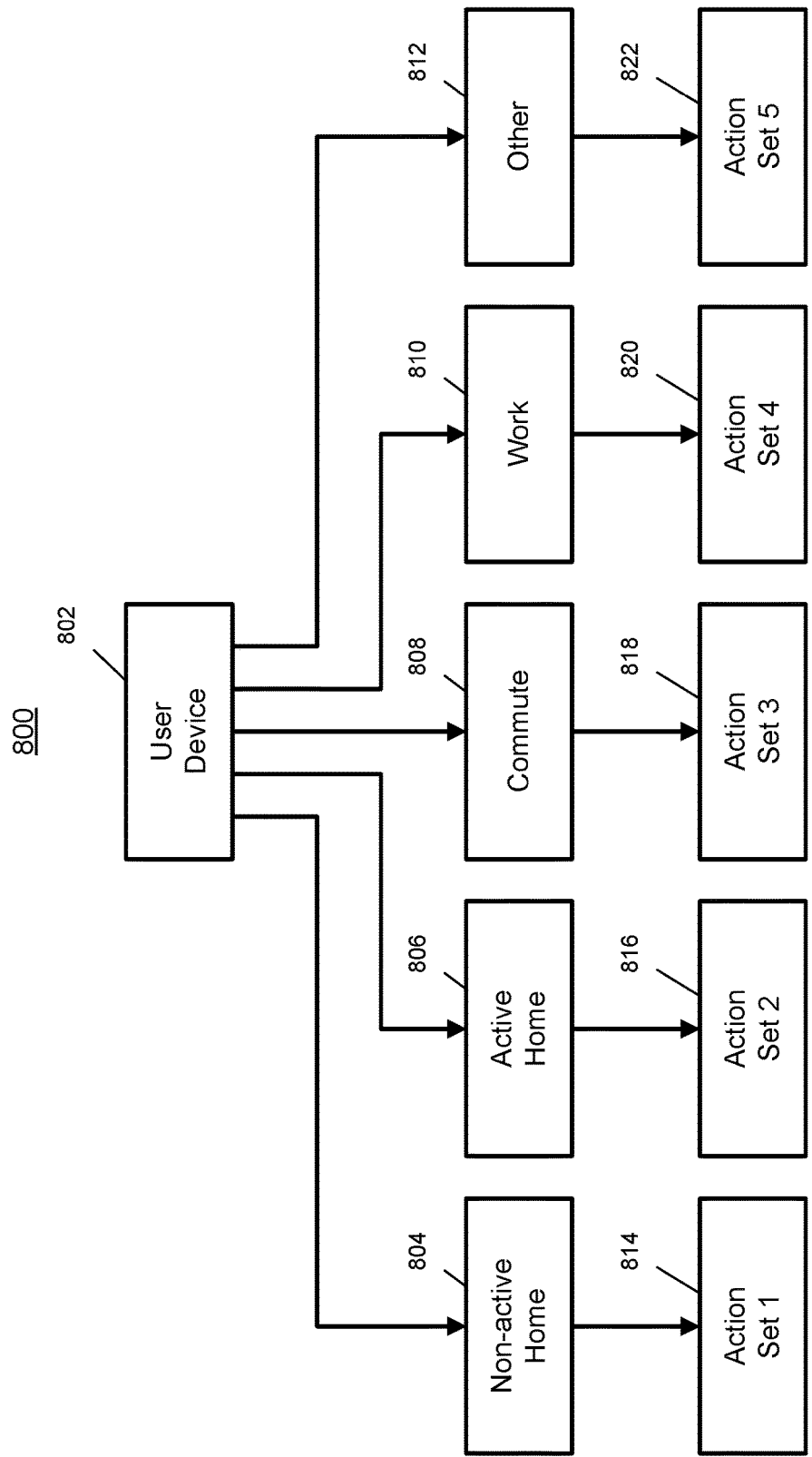
FIG. 8 depicts a block diagram of an example activity state tree according to example embodiments of the present disclosure.

FIG. 8 depicts an example action set determination system 800. The user device 802, or user computing system, can include one or more sensors for receiving touch inputs and may be part of a user computing system that includes one or more activity sensors for obtaining or generating activity data. The activity data can be descriptive and/or indicative of a particular activity state. The user device 802, or user computing system, can obtain the activity data, process the activity data, determine an activity state based on the activity data, and determine an action set associated with the activity state. For example, the one or more activity sensors can obtain movement data from one or more inertial sensors. The user computing system can process the movement data to determine an activity level. If the activity level is a low activity level, a first action set 814 may be determined, and if the activity level is a high activity level, a second action set 816 may be determined. In some implementations, a high activity level may be determined by movement data, motion data, or accelerometer data being descriptive of activity above a threshold. In some implementations, a low activity level may be determined by movement data, motion data, or accelerometer data being descriptive of activity below a threshold. The threshold may be an active versus non-active threshold. In some implementations, the threshold may be predefined, manually defined, or may be a machine-learned threshold (e.g., a user's average heart rate or average activity level may be determined and used to determine a threshold indicative of a high activity level). The threshold may be user specific or may be based on a globally defined threshold.

Another example can involve a time of day or time of week. For example, a user may complete a set of actions repeatedly at a certain time of day, or a user may manually generate an action set for a certain time of day or a certain time of week, month, year, etc. The user computing system can generate or obtain activity data descriptive of a time. In some implementations, the time can be determined to be the time of the day associated with a certain set of actions. For example, during a user's commute 808, the user may select a certain set of actions. Therefore, if the user computing system determines the time is the commuting time 808, the third action set 818 may be determined.

Another example can involve obtaining activity data descriptive of a user device 802 location. The activity data can include GPS data that can be processed to determine the user is at work 810. In response to the user device being at the work location 810, the fourth action set 820 can be determined. In some implementations, the activity data can include both movement data and location data to provide more tailored action sets. For example, an activity level can be determined along with a location being determined, such that a non-active home activity state 804 can be determined or an active home activity state 806 can be determined. The non-active home activity state 804 can be associated with the first action set 814, and the active home activity state 806 can be associated with the second action set 816.

In some implementations, the corpus of possible activity states can include a plurality of other activity states 812 associated with a plurality of other action sets, such as fifth action set 822. The activity data can include motion data, location data, time data, weather data, device-specific data, etc. The one or more activity sensors can include inertial sensors, location sensors, internal clocks, thermometer sensors, pressure sensors, transmitters, etc. For example, in some implementations, metadata can be sent to the user device indicative of a device being communicatively connected to a certain type of device. Based on the determined type of device, a certain action set can be determined. For example, a music playing device can be associated with a music player action set including volume control, song/channel control, and/or play/pause control. Moreover, for devices with a plurality of functions, an action set may be determined based on an open application or a most recently used function.

Each of the action sets can be associated with the same or partially overlapping gestures, such that a single gesture can cause different actions dependent on the determined activity state.

Figure 9:
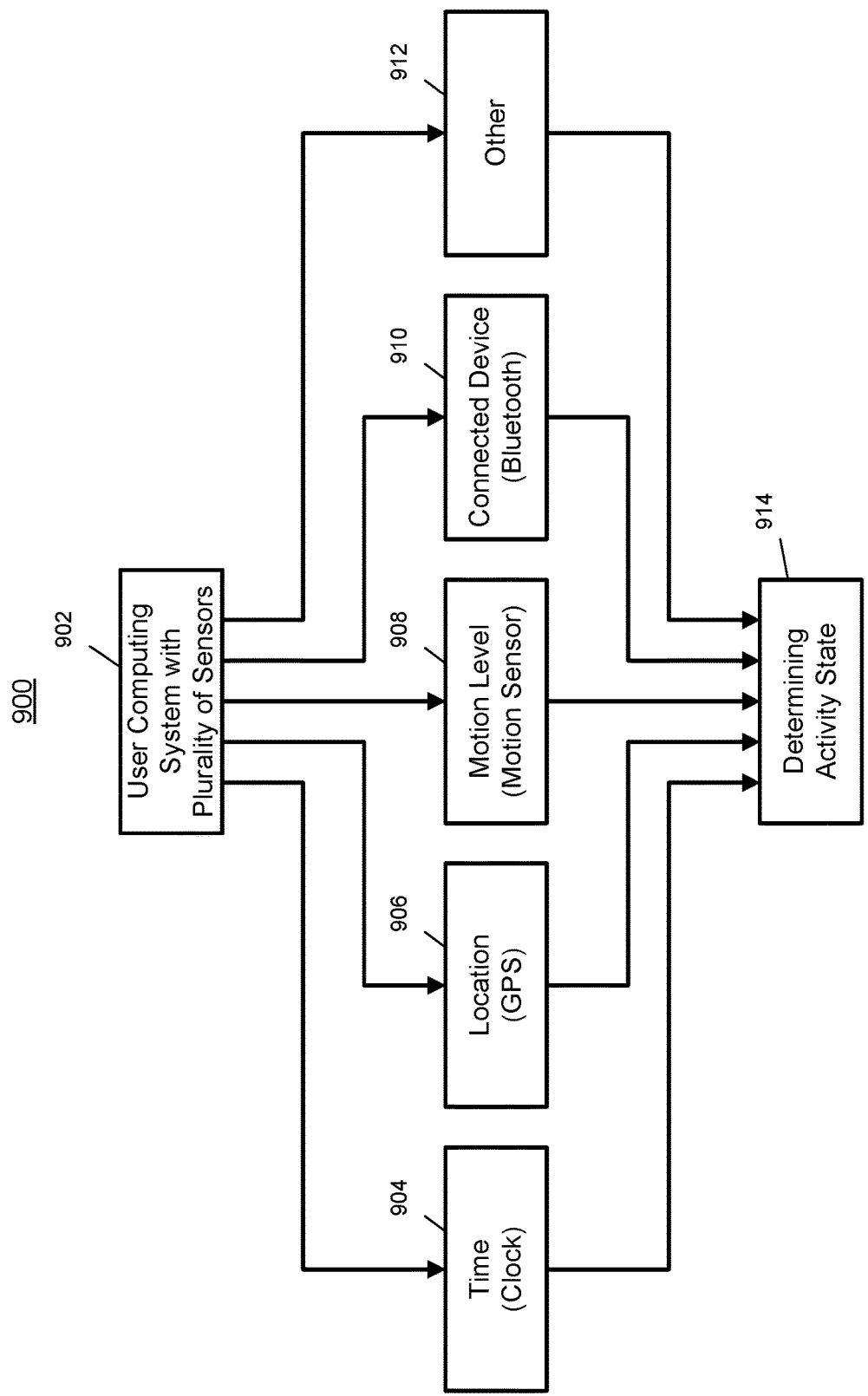
FIG. 9 depicts a block diagram of an example activity state determination system according to example embodiments of the present disclosure.

FIG. 9 depicts an example activity state determination system 900 according to the systems and methods disclosed herein. The system 900 can include a user computing system 802 that includes a plurality of sensors. The plurality of sensors can include one or more touch sensors and one or more activity sensors. The activity sensors can include time sensors (e.g., an internal clock) 904, location sensors (e.g., a GPS locator) 906, motion sensors (e.g., inertial sensors) 908, wireless transmitters (e.g., a Bluetooth transmitter) 910, and/or other sensors (e.g., image sensors, audio sensors, etc.) 912. The one or more activity sensors can be used to determine an activity state 914.

For example, the time sensors 904 can generate time data that can be processed to determine a time (e.g., the time of day in which the user usually listens to music), which may cause a certain action set (e.g., a plurality of music player actions) to be selected based on the time activity state. Another example can involve location data. The location data may be processed to determine the user is at work. Based on the user being at work a certain action set can be determined, such that the work action set is different from the home action set.

Moreover, in some implementations, the activity state can be determined based on activity data that includes data generated by multiple sensors of multiple sensor types. For example, an active home activity state can be determined based on location data indicative of the user's home and motion data that is descriptive of motion above a determined threshold.

Figure 10:
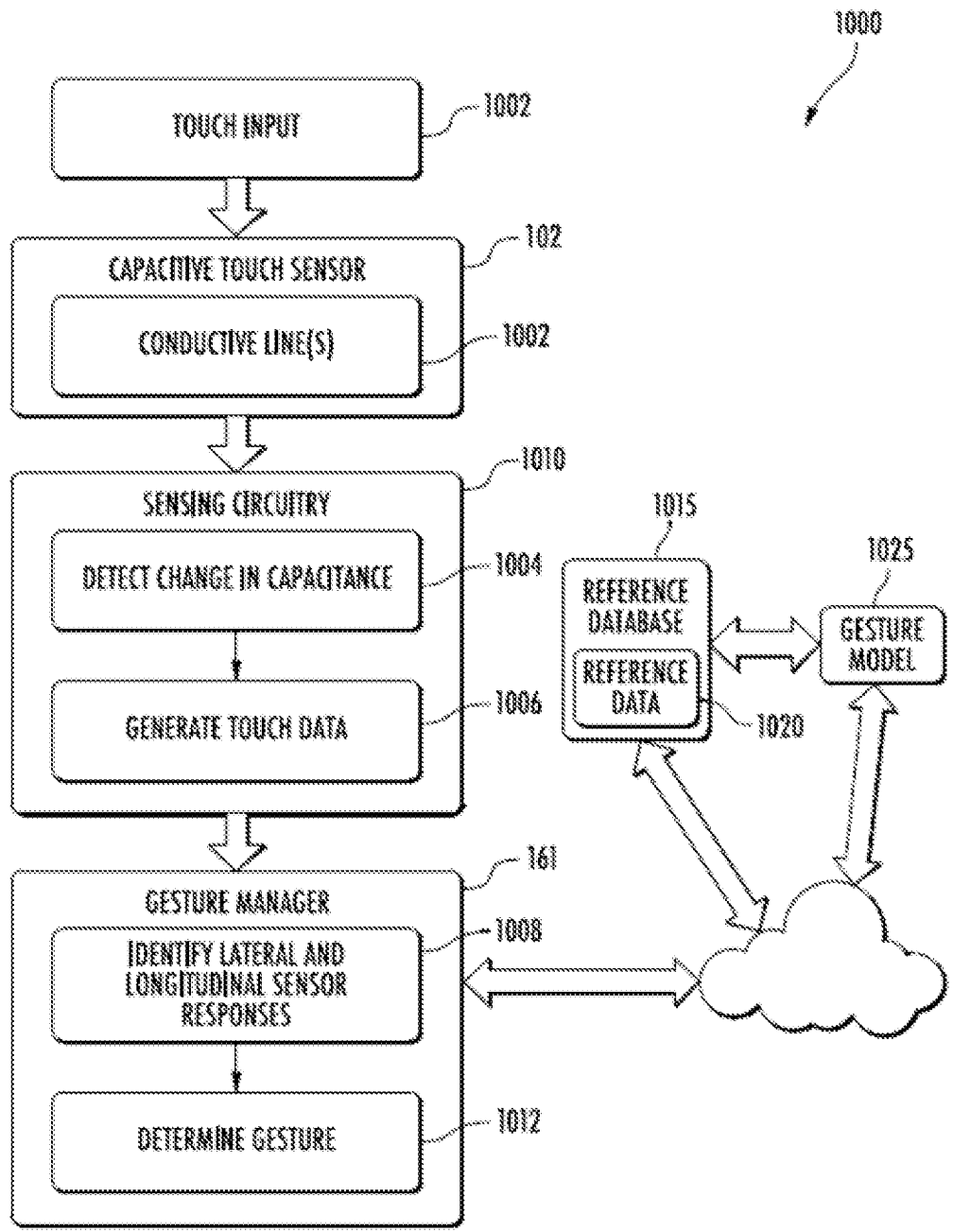
FIG. 10 is a block diagram depicting an example computing environment 1000, illustrating the detection of gestures based on an identified input location of a touch sensor in accordance with example embodiments of the present disclosure.

FIG. 10 is a block diagram depicting an example computing environment 1000, illustrating the detection of gestures based on an identified input location of a touch sensor in accordance with example embodiments of the present disclosure.

Interactive object 104 and/or one or more computing devices in communication with interactive object 104 can detect a user gesture based at least in part on capacitive touch sensor 102. For example, interactive object 104 and/or the one or more computing devices can implement a gesture manager 161 that can identify one or more gestures in response to touch input 1002 to the capacitive touch sensor 102.

Interactive object 104 can detect touch input 1002 to capacitive touch sensor 102 based on a change in capacitance associated with a set of conductive threads 210. For example, a user can move an object (e.g., finger, conductive stylus, etc.) proximate to or touch capacitive touch sensor 102, causing a response by the individual sensing elements. By way of example, the capacitance associated with each sensing element can change when an object touches or comes in proximity to the sensing element. As shown at (1004), sensing circuitry 126 can detect a change in capacitance associated with one or more of the sensing elements. Sensing circuitry 126 can generate touch data at (1006) that is indicative of the response (e.g., change in capacitance) of the sensing elements to the touch input. The touch data can include one or more touch input features associated with touch input 1002. In some examples, the touch data may identify a particular element, and an associated response such as a change in capacitance. In some examples, the touch data may indicate a time associated with an element response.

Gesture manager 161 can analyze the touch data to identify the one or more touch input features associated with touch input 1002. Gesture manager 161 can be implemented at interactive object 104 (e.g., by one or more processors of internal electronics module 124 and/or removable electronics module 206) and/or one or more computing devices remote from the interactive object 104.

Gesture manager 161 can analyze the touch data at (1008) to identify one or more sensor responses. For example, a lateral sensor response, longitudinal sensor response, or combination of sensor responses can be determined in example embodiments. By way of example, gesture manager 161 can determine at least one signal difference associated with a sensing line in a plurality of first conductive sensing elements coupled to a first surface of the flexible substrate and one signal difference associated with a sensing line in a plurality of second conductive sensing elements coupled to either a first or second surface of the flexible substrate. If the signal difference of the sensing line in a plurality of second conductive sensing elements is within a predetermined threshold range of the signal difference of the sensing line in a plurality of first conductive sensing elements, the gesture manager 161 can determine that the touch input is associated with a first sensing subregion of the flexible substrate rather than a second sensing subregion. However, if the signal difference exceeds a predetermined threshold value, the gesture manager 161 can determine that the touch input was received at the second sensing subregion.

In accordance with some implementations, the one or more control circuits can analyze a respective response such as a resistance or capacitance of each sensing element of the touch sensor to determine whether a touch input is associated with a first sensing subregion of the touch sensor or a second subregion of the touch sensor.

Gesture manager 161 can determine a gesture based at least in part on the touch data. In some examples gesture manager 161 may identify a particular gesture based on the surface of which the touch input is received. For example, a first gesture may be identified in response to a touch input at a first surface while a second gesture may be identified in response to a touch input at a second surface.

In some examples, gesture manager 161 can identify at least one gesture based on reference data 1020. Reference data 1020 can include data indicative of one or more predefined parameters associated with a particular input gesture. The reference data 1020 can be stored in a reference database 1015 in association with data indicative of one or more gestures. Reference database 1015 can be stored at interactive object 104 (e.g., internal electronics module 124 and/or removable electronics module 206) and/or at one or more remote computing devices in communication with the interactive object 104. In such a case, interactive object 104 can access reference database 1015 via one or more communication interfaces (e.g., network interface 162).

Gesture manager 161 can compare the touch data indicative of the touch input 1002 with reference data 1020 corresponding to at least one gesture. For example, gesture manager 161 can compare touch input features associated with touch input 1002 to reference data 1020 indicative of one or more pre-defined parameters associated with a gesture. Gesture manager 161 can determine a correspondence between at least one touch input feature and at least one parameter. Gesture manager 161 can detect a correspondence between touch input 1002 and at least one line gesture identified in reference database 1015 based on the determined correspondence between at least one touch input feature and at least one parameter. For example, a similarity between the touch input 1002 and a respective gesture can be determined based on a correspondence of touch input features and gesture parameters.

In some examples, gesture manager 161 can input touch data into one or more machine learned gesture models 1025. A machine-learned gesture model 1025 can be configured to output a detection of at least one gesture based on touch data and/or an identification of a surface or subset of sensing element associated with a touch input. Machine-learned gesture models 1025 can generate an output including data indicative of a gesture detection. For example, machine learned gesture model 1025 can be trained, via one or more machine learning techniques, using training data to detect particular gestures based on touch data. Similarly, a machine learned gesture model 1025 can be trained, via one or more machine learning techniques, using training data to detect a surface associated with a touch input.

Gesture manager 161 can input touch data indicative of touch input 1002 and/or into machine learned gesture model 1025. One or more gesture models 1025 can be configured to determine whether the touch input is associated with a first subset of sensing elements or a second subset of sensing elements. Additionally or alternatively, one or more gesture models 1025 can be configured to generate one or more outputs indicative of whether the touch data corresponds to one or more input gestures. Gesture model 1025 can output data indicative of a particular gesture associated with the touch data. Additionally, or alternatively, gesture model 1025 can output data indicative of a surface associated with the touch data. Gesture model 1025 can be configured to output data indicative of an inference or detection of a respective gesture based on a similarity between touch data indicative of touch input 1002 and one or more parameters associated with the gesture.

In accordance with examples embodiments, a sensor system can selectively determine whether a touch input corresponds to a particular input gesture based at least in part on whether the touch input is determined to have been received at a first sensing subregion of the flexible substrate or a second subregion of the flexible substrate. In response to determining that the touch input is associated with the first subregion, the sensor system can determine whether the touch data corresponds to one or more gestures or other predetermined movements. For example, the sensor system can compare the touch data with reference data representing one or more predefined parameters to determine if the touch data corresponds to one or more gestures. In response to detecting the first input gesture, the sensor system can initiate a functionality at a computing device. In response to determining that the touch input is associated with the second surface, however, the sensor system can automatically determine that the touch input is not indicative of the particular input gesture such that a functionality is not initiated.

In some implementations, a touch input at the first surface of the touch sensor can be associated with a first input gesture while the same or a similar touch input at a second surface of the touch sensor can be associated with a second input gesture. For example, the sensor system can determine whether touch data generated in response to a touch input is associated with the first surface of the touch sensor or the second surface of the touch sensor. Additionally, the sensor system can determine whether the touch data corresponds to one or more predefined parameters. If the touch data corresponds to the one or more predefined parameters and is associated with the first sensing subregion the sensor system can determine that a first input gesture has been performed. If, however, the touch data corresponds to the one or more predefined parameters and is associated with the second sensing subregion, the sensor system can determine that a second input gesture has been performed. By differentiating the sensing subregion at which an input is received, the sensor system can detect a larger number of input gestures in example embodiments.

Interactive object 104 and/or a remote computing device in communication with interactive object 104 can initiate one or more actions based on a detected gesture. For example, the detected gesture can be associated with a navigation command (e.g., scrolling up/down/side, flipping a page, etc.) in one or more user interfaces coupled to interactive object 104 (e.g., via the capacitive touch sensor 102, the controller, or both) and/or any of the one or more remote computing devices. In addition, or alternatively, the respective gesture can initiate one or more predefined actions utilizing one or more computing devices, such as, for example, dialing a number, sending a text message, playing a sound recording etc.

Figure 11:
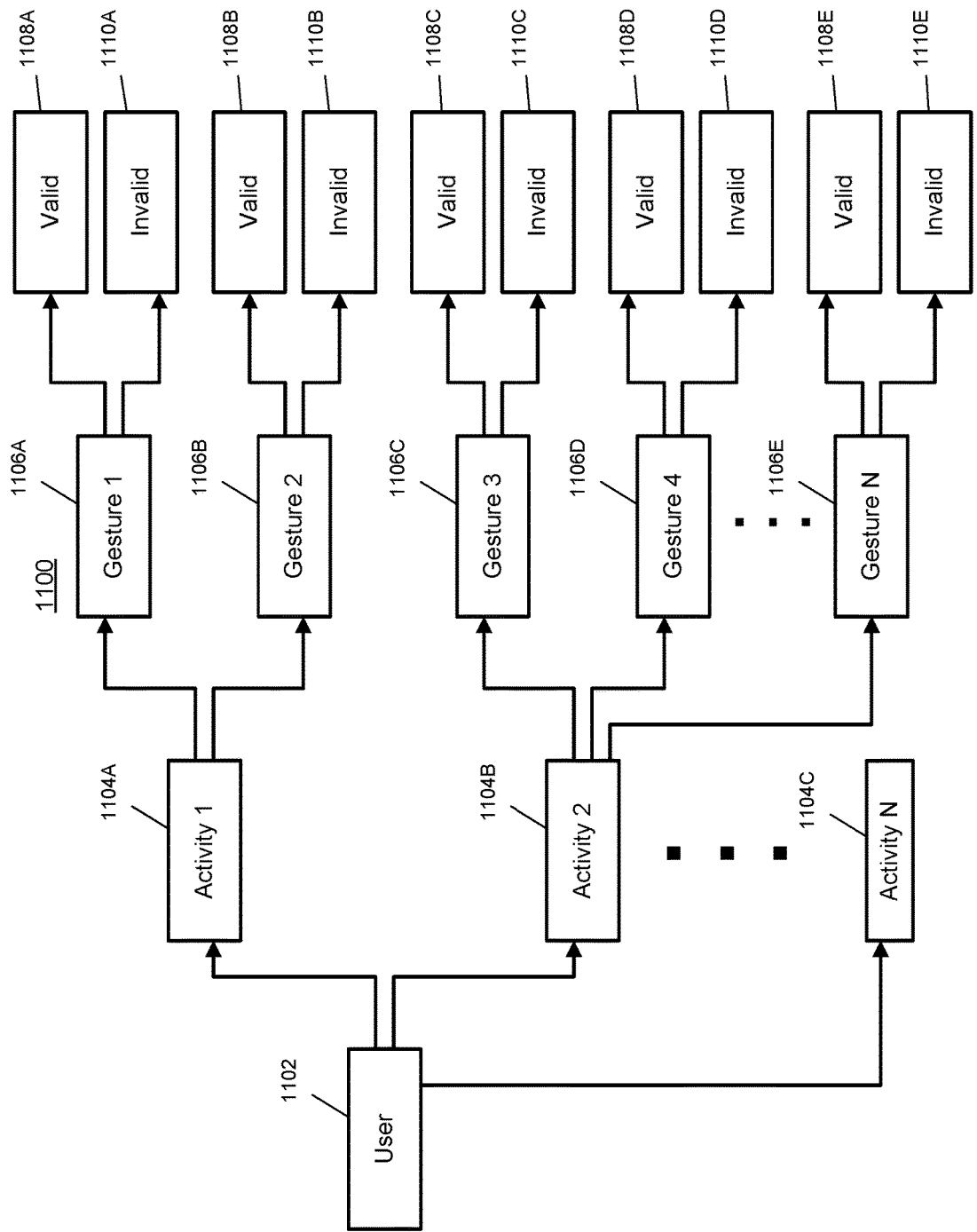
FIG. 11 depicts a block diagram of an example gesture tree according to example embodiments of the present disclosure.

FIG. 11 depicts an example audio feedback determination tree 1100 according to systems and methods disclosed herein. The determination tree 1100 can be user 1102 dependent such that the activity states, gesture sets, and/or the action sets can be user-specific. Alternatively, in some implementations, the activity states, gesture sets, and/or the action sets may be the same for a plurality of users. The user computing system 1102 can include one or more activity sensors to determine activity states 1104. For example, a first activity state 1104A can be determined based on the activity data. The first activity state 1104A can be associated with an action set associated with a first gesture 1106A and a second gesture 1106B. A plurality of activity states 1104 associated with a plurality of action sets may be determined, including a second activity state 1104B and an nth activity state 1104C. The second activity state 1104B can be associated with a plurality of actions associated with a plurality of gestures 1106 including a third gesture 1106C, a fourth gesture 1106D, and an nth gesture 1106E. Additionally and/or alternatively, the second activity state 1104B can include an action associated with either the first gesture 1106A or the second gesture 1106B.

The systems and methods disclosed herein can include an audio notification being determined and provided in response to a change in activity state. For example, when a first activity state 1104A is determined, a specific sound can play, and a different sound may be played in response to a second activity state 1104B being determined.

Each gesture 1106 can include a different valid audio feedback 1108. For example, the system may process the input data to determine if the gesture is a valid gesture associated with the activity state 1104. For example, when a successful first gesture 1106A is completed, a first sound 1108A may be played with the valid determination. If the gesture is determined to be invalid, a second sound 1110A may be provided. Similarly, when a successful second gesture 1106B is completed, a third sound 1108B may be played with the valid determination. If the gesture is determined to be invalid, a fourth sound 1110B may be provided. In some implementations, the invalid feedback 1110 can be the same for all gestures 1106 associated with a certain activity state 1104. However, the valid feedback 1108 for each gesture can be different regardless of the activity state 1104.

In some implementations, the valid feedback 1108C for the third gesture 1106C can include a harmonious sound, and the invalid feedback 1110C for the third gesture 1106C can include a discordant sound. Additionally and/or alternatively, the invalid feedback 1110D for the fourth gesture 1106D can include a haptic feedback. In some implementations, the valid feedback 1108D for the fourth gesture 1106D can include a sound in the same musical key as the valid feedback 1108C for the third gesture 1106C.

In some implementations, the valid feedback 1108E and/or the invalid feedback 1110E for the nth gesture 1106E may be based at least in part on the one or more sensing lines contacted during the gesture. For example, the systems and methods can include providing line-specific audio feedback, and the valid feedback 1108E can include a repetition of at least one of the line-specific audio feedbacks, while the invalid feedback 1110E may include an off-key sound when compared to the line-specific audio feedback.

Figure 12:
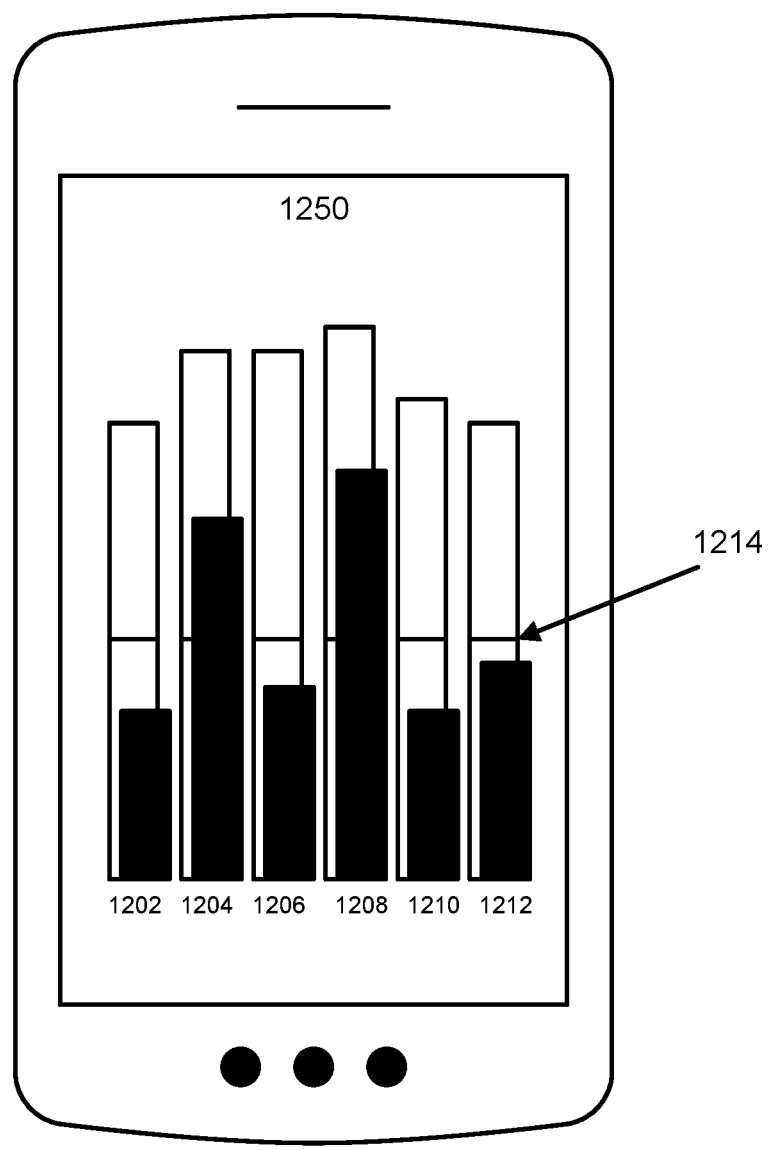
FIG. 12 depicts a block diagram of an example thread visualizer application according to example embodiments of the present disclosure.

FIG. 12 depicts an example thread visualizer application 1200. The thread visualizer application 1200 can be utilized to further aid in training a user to provide valid gestures. The thread visualizer application 1200 can be downloaded and accessed on a mobile computing device or any computing device. The thread visualizer application 1200 can include a visual interface 1250 that can include a plurality of bars representing a plurality of sensing lines. A first set of bars can be superimposed over a second set of bars. The first set of bars can be indicative of at least one of a pressure level or a capacitance level for each respective sensing line during a period of time (e.g., half a second, two seconds, ten seconds, etc.). The second set of bars can represent a normalized maximum for each respective sensing line. In some implementations, the second set of bars can include bars of equal size or different sizes. Additionally and/or alternatively, a threshold line 1214 can be displayed on each bar of the second set of bars to display the threshold pressure for which a touch input would be registered. In some implementations, the threshold 1214 can be the same for each sensing line. However, in some implementations, the threshold 1214 may vary for each sensing line.

The depicted visual display 1250 in FIG. 12 represents six sensing lines. In the depicted example, the visual display 1250 indicates that a touch input is registered for two sensing lines (i.e., 1204 and 1208). The other four sensing lines (i.e., 1202, 1206, 1210, and 1212) do not register a touch input despite some pressure being registered. The visual display 1250 can update in real-time to provide real-time data on registered inputs. The audio feedback determination system along with the thread visualizer application 1200 can provide real-time feedback that can help train or reinforce how gestures should be input for certain actions.

Figure 13:
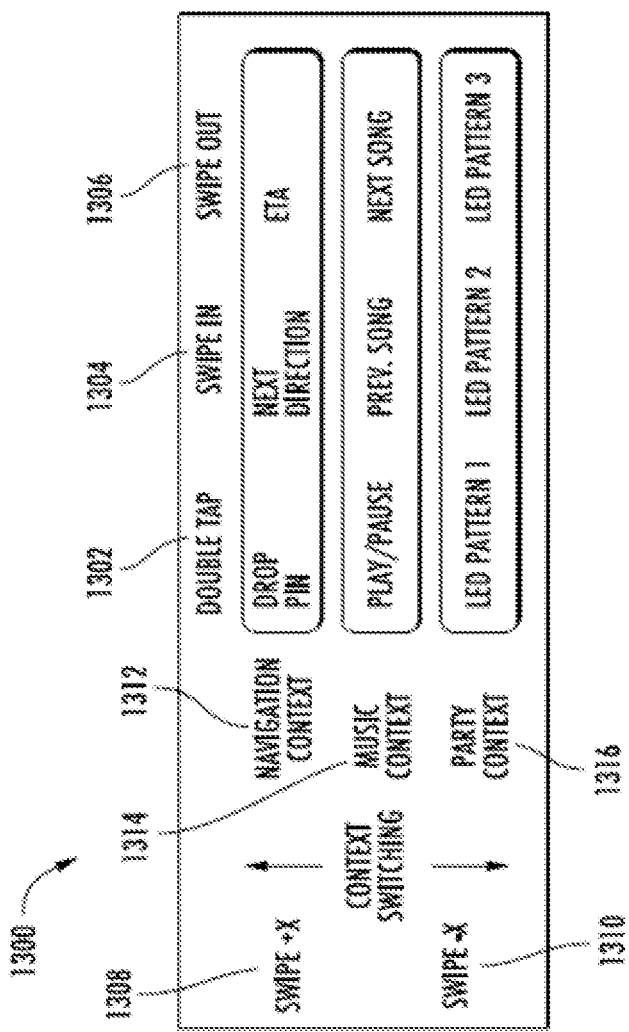
FIG. 13 is a diagram depicting a context switching system for touch inputs in accordance with example embodiments of the present disclosure.

FIG. 13 is a diagram depicting a context switching system for touch inputs in accordance with example embodiments of the present disclosure. In this example, a context switching system 1300 can have a number of associated gestures that it can detect. For example, the gestures can include swiping in the +x direction 1308, swiping in the −x direction 1310, double tapping 1302, swiping in 1304, and swiping out 1306. Each gesture can be associated with a particular action. However, given that the number of actions that may be desired can exceed the number of gestures that can be detected, the context switching system 1300 can enable several different contexts. Each context can associate one or more gestures with different actions based on the current context. Example contexts can include a navigation context 1312, a music context 1314, and a party context 1316.

In some examples, one or more gestures can be associated with switching contexts. In this example, the swipe +x 1308 and the swipe −x 1310 gestures can be associated with switching from one context to another. Once a context is selected, the specific actions associated with particular gestures can be based on the associated context. For example, in the navigation context 1312, the double tap gestures 1302 can be associated with a drop pin action, the swipe in gesture 1304 can be associated with a next direction action, the swipe out gesture 1306 is associated with an eta action.

Figure 14:
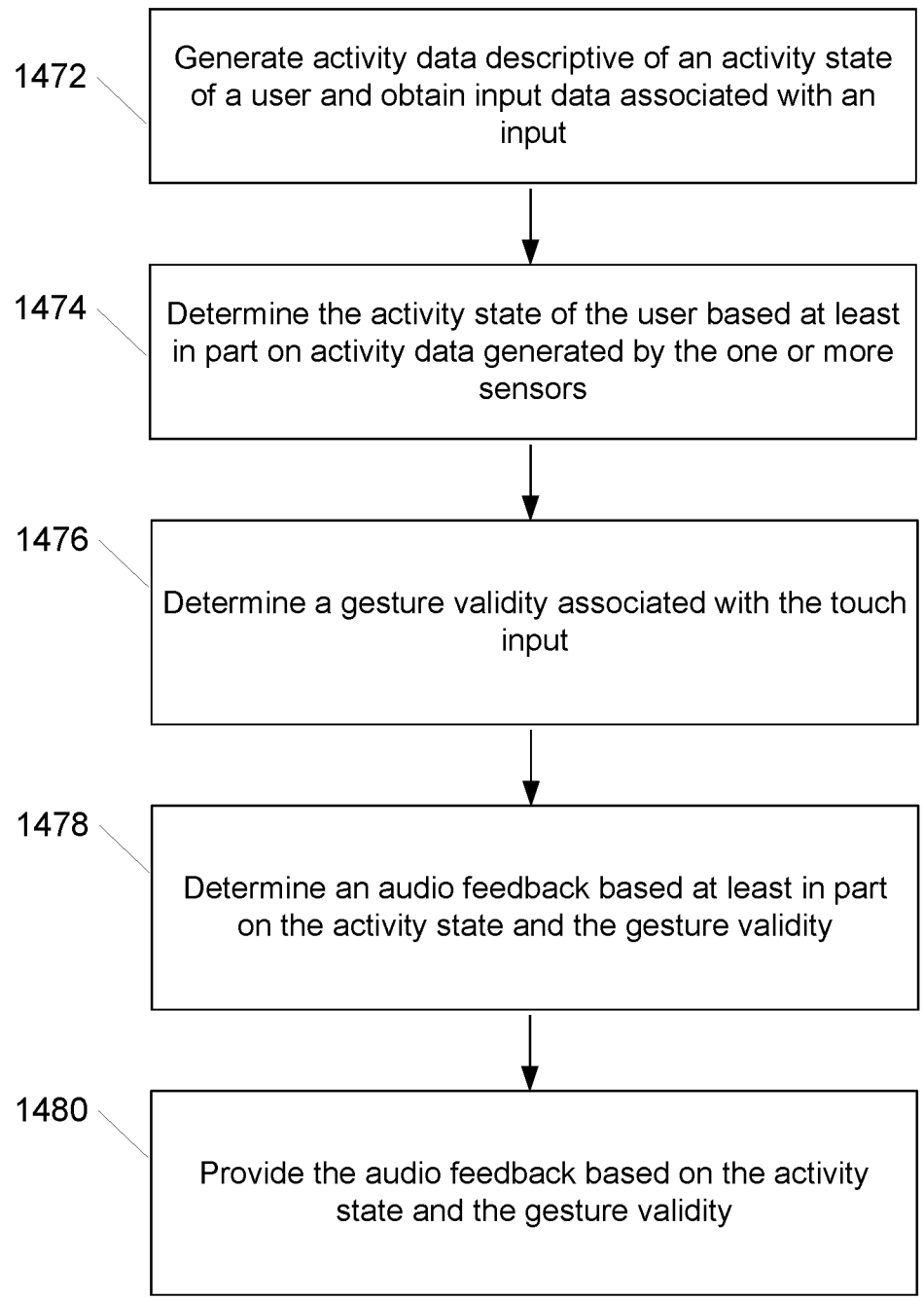
FIG. 14 depicts a flow chart diagram of an example method to perform providing audio feedback in response to an activity state and user input according to example embodiments of the present disclosure.

FIG. 14 depicts a flow chart diagram of an example method to perform according to example embodiments of the present disclosure. Although FIG. 14 depicts steps performed in a particular order for purposes of illustration and discussion, the methods of the present disclosure are not limited to the particularly illustrated order or arrangement. The various steps of the method 1400 can be omitted, rearranged, combined, and/or adapted in various ways without deviating from the scope of the present disclosure.

At 1472, a computing system can generate activity data descriptive of an activity state of a user and obtain input data associated with an input. The activity data can be generated by one or more activity sensors in a computing system. The one or more activity sensors can include one or more motion sensors, one or more location sensors, one or more time sensors, and/or one or more proximity sensors. In some implementations, the input data can include touch data associated with one or more touch inputs. Moreover, the touch data can be obtained in response to one or more touch inputs being obtained by one or more touch sensors in a computing system. The one or more touch sensors can include a plurality of sensing lines. The sensing lines can be included in a smart wearable and may be cylindrical in shape. Alternatively and/or additionally, the input data can be descriptive of inputs detected in a variety of manners with a variety of sensors. For example, in some implementations, the input can be a motion gesture that may be detected using one or more inertial sensors. The input data may be of an input detected by processing image data from an image sensor to detect the input. The input can be a hand wave, eye movement, blinking, finger movement, or mouth movements. In some implementations, the input data can include audio data descriptive of human speech generated using one or more audio sensors.

At 1474, the computing system can determine the activity state of the user based at least in part on activity data generated by the one or more sensors. The activity state can be an activity level (e.g., active, non-active, high activity level, or low activity level) in which the activity level is determined based on a user's pulse or based on motion data generated with an inertial sensor. Alternatively and/or additionally, the activity state can be a time or a location determined using activity data generated by one or more activity sensors.

At 1476, the computing system can determine a gesture validity associated with the touch input. Determining gesture validity can involve determining an action set is associated with the activity state, and then determining if the input is associated with any of the gestures associated with the action set. If the input is associated with any of the gestures, the gesture is valid. If they are not associated or matching, then the gesture is invalid.

At 1478, the computing system can determine an audio feedback based at least in part on the activity state and the gesture validity. In some implementations, an audio feedback for a valid gesture can be harmonious, while an audio feedback for an invalid gesture can be discordant. The audio feedback may be different for each activity state.

At 1480, the computing system can provide the audio feedback based on the activity state and the gesture validity. The audio feedback can be provided with one or more audio output devices in the computing system.

Figure 15:
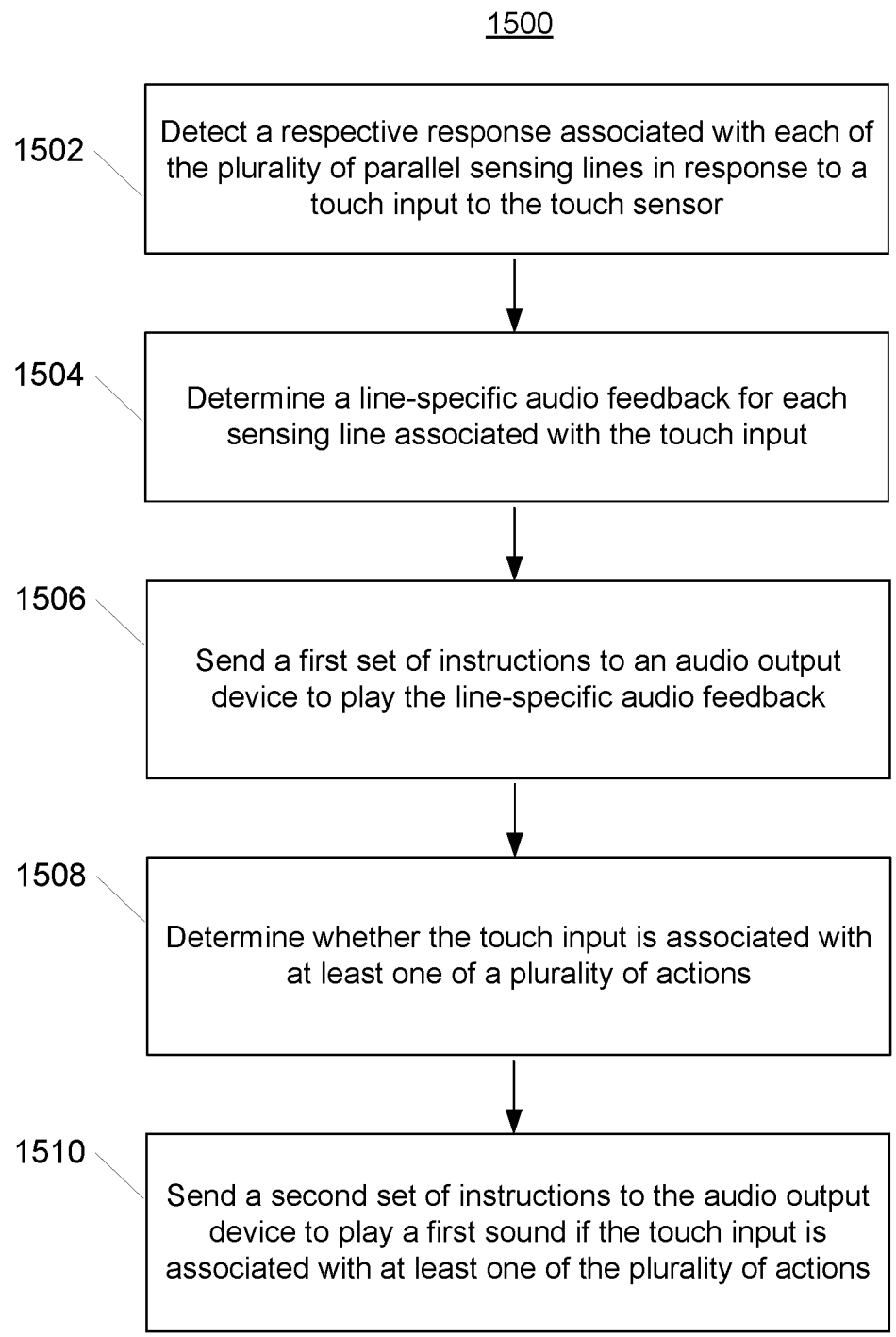
FIG. 15 depicts a flow chart diagram of an example method to perform providing line-specific audio feedbacks according to example embodiments of the present disclosure.

FIG. 15 depicts a flow chart diagram of an example method to perform according to example embodiments of the present disclosure. Although FIG. 15 depicts steps performed in a particular order for purposes of illustration and discussion, the methods of the present disclosure are not limited to the particularly illustrated order or arrangement. The various steps of the method 1500 can be omitted, rearranged, combined, and/or adapted in various ways without deviating from the scope of the present disclosure.

At 1502, a computing system can detect a respective response associated with each of the plurality of parallel sensing lines in response to a touch input to the touch sensor.

At 1504, the computing system can determine a line-specific audio feedback for each sensing line associated with the touch input. The line-specific audio feedback may be determined by accessing a directory or database of sounds associated with the specific sensing line. In some implementations, the line-specific audio feedback may be based at least in part on a determined activity state. Additionally, in some implementations, each line-specific audio feedback for the plurality of sensing lines may have a common musical key but a different musical note.

At 1506, the computing system can send a first set of instructions to an audio output device to play the line-specific audio feedback. The first set of instructions can be sent to have the line-specific audio feedback provided in real-time to provide real-time feedback to a user. In some implementations, the line-specific audio feedback may mimic sounds from a musical instrument (e.g., a guitar, a banjo, a ukulele, a piano, etc.).

At 1508, the computing system can determine whether the touch input is associated with at least one of a plurality of actions. The plurality of actions may be a plurality of actions associated with a determined activity state (e.g., a high activity level or a user being at home). The plurality of actions can be associated with a plurality of gestures, and determining whether the touch input is associated with at least one of a plurality of actions can include determining whether the touch input is associated with at least one of the plurality of gestures.

At 1510, the computing system can send a second set of instructions to the audio output device to play a first sound if the touch input is associated with at least one of the plurality of actions. If the touch input is not associated with at least one of the plurality of actions, a second set of instructions can be sent to the audio output device to provide a second sound and/or provide haptic feedback. In some implementations, the first sound may include at least a portion of the line-specific audio feedback.

Figure 16:
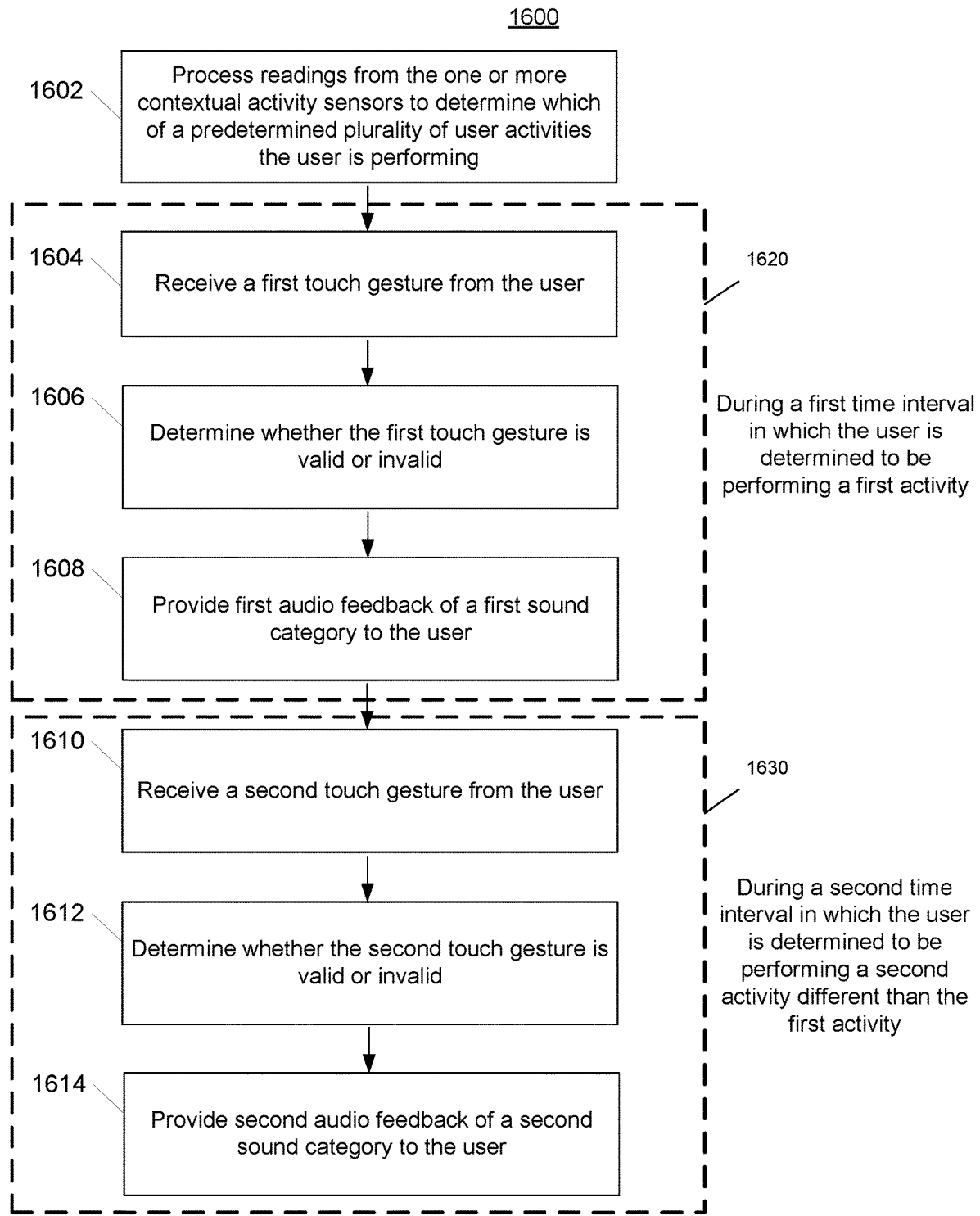
FIG. 16 depicts a flow chart diagram of an example method to perform providing an audio feedback based on gesture validity according to example embodiments of the present disclosure.

FIG. 16 depicts a flow chart diagram of an example method to perform according to example embodiments of the present disclosure. Although FIG. 16 depicts steps performed in a particular order for purposes of illustration and discussion, the methods of the present disclosure are not limited to the particularly illustrated order or arrangement. The various steps of the method 1600 can be omitted, rearranged, combined, and/or adapted in various ways without deviating from the scope of the present disclosure.

At 1602, a computing system can process readings from the one or more contextual activity sensors to determine which of a predetermined plurality of user activities the user is performing. The one or more contextual activity sensors can include a plurality of sensor types and may be used to determine a plurality of user activity types (e.g., an activity level, a time of day, a location, or a connected device).

During a first time interval in which the user is determined to be performing a first activity, the computing system can complete a first set of operations.

At 1604, the computing system can receive a first touch gesture from the user. The first touch gesture can include individual sensing line compressions, a swipe gesture, and/or a timed compression.

At 1606, the computing system can determine whether the first touch gesture is valid or invalid. Determination of the validity of the gesture can include determining the gesture set associated with the action set for the first activity. The first touch gesture can then be compared to the gesture set to determine if the first touch gesture matches any of the touch gestures in the gesture set. If the first touch gesture matches one or more gestures in the gesture set, the first touch gesture is determined to be valid.

At 1608, the computing system can provide first audio feedback of a first sound category to the user. The first audio feedback can include a first sound if the first gesture is valid or can include a second sound if the first gesture is invalid. The first sound can be harmonious, while the second sound can be discordant.

During a second time interval in which the user is determined to be performing a second activity different than the first activity, the computing system can complete a second set of operations.

At 1610, the computing system can receive a second touch gesture from the user. The second touch gesture can include individual sensing line compressions, a swipe gesture, and/or a timed compression.

At 1612, the computing system can determine whether the second touch gesture is valid or invalid. Determination of the validity of the gesture can include determining the gesture set associated with the action set for the second activity. The second touch gesture can then be compared to the gesture set to determine if the second touch gesture matches any of the touch gestures in the gesture set. If the second touch gesture matches one or more gestures in the gesture set, the second touch gesture is determined to be valid.

At 1614, the computing system can provide second audio feedback of a second sound category to the user. The second audio feedback can include a third sound if the second gesture is valid or can include a fourth sound if the second gesture is invalid. The third sound can be harmonious, while the fourth sound can be discordant. The first sound, the second sound, the third sound, and the fourth sound can all be different sounds.

Figure 17:
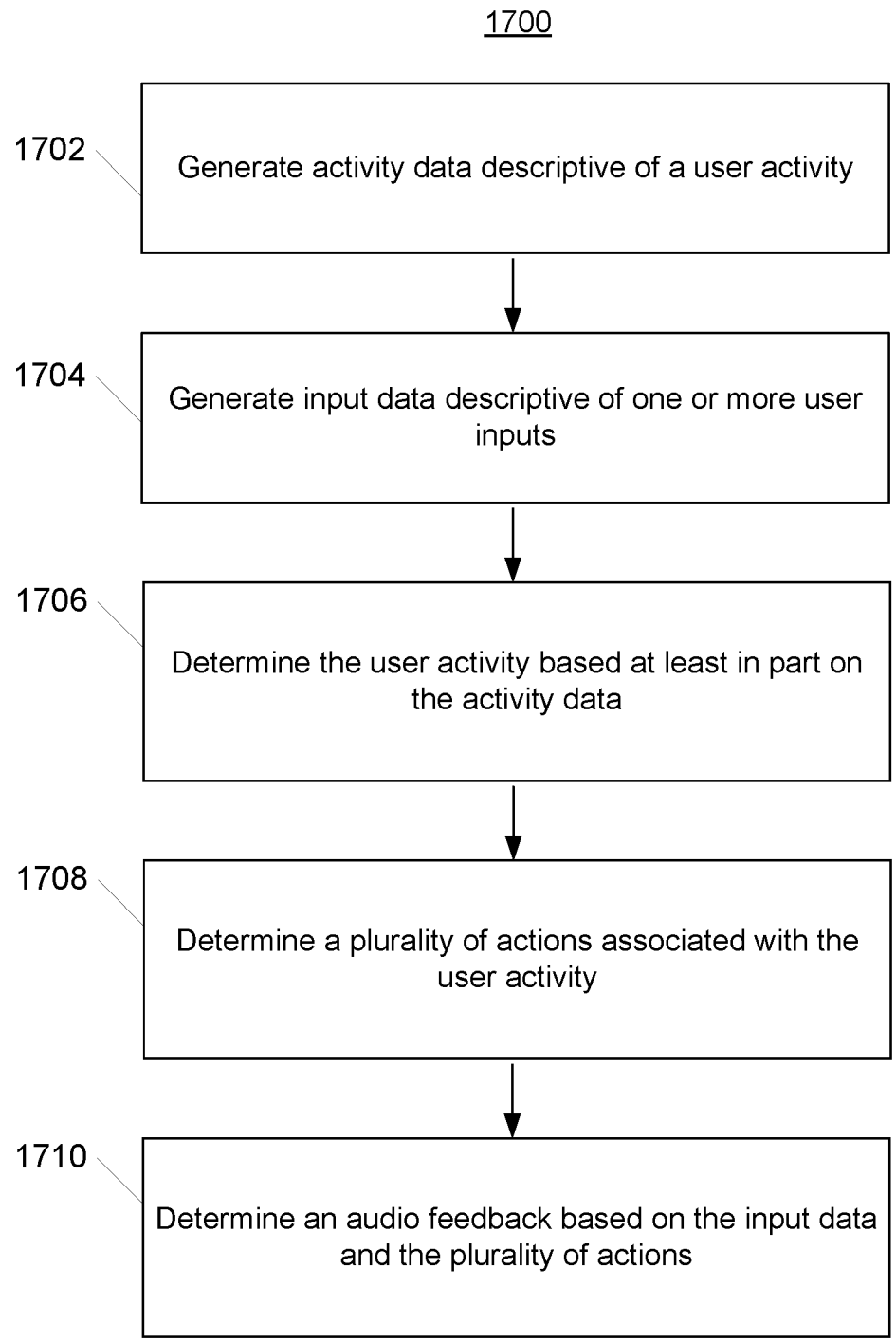
FIG. 17 depicts a flow chart diagram of an example method to perform determining an audio feedback based on activity data and input data according to example embodiments of the present disclosure.

FIG. 17 depicts a flow chart diagram of an example method to perform according to example embodiments of the present disclosure. Although FIG. 17 depicts steps performed in a particular order for purposes of illustration and discussion, the methods of the present disclosure are not limited to the particularly illustrated order or arrangement. The various steps of the method 1700 can be omitted, rearranged, combined, and/or adapted in various ways without deviating from the scope of the present disclosure.

At 1702, a computing system can generate activity data descriptive of a user activity. The activity data can be generated continuously and stored for a brief period of time or may be generated in response to a trigger event (e.g., a speech input, a device pairing, a touch input, etc.).

At 1704, the computing system can generate input data descriptive of one or more user inputs. The one or more user inputs can include a speech input, a touch input, and/or a visual input.

At 1706, the computing system can determine the user activity based at least in part on the activity data. The determination of the user activity can include using a machine-learned model trained to determine user activities.

At 1708, the computing system can determine a plurality of actions associated with the user activity. The plurality of actions can be actions manually associated with the user activity via a predefined user setting or via user inputs. In some implementations, the plurality of actions can be associated with the user activity based on historical data. The historical data can include data indicative of the actions most commonly selected during a respective user activity. The plurality of actions can be stored with associated sounds and associated activity states.

At 1710, the computing system can determine an audio feedback based on the input data and the plurality of actions. The audio feedback can be different for each respective action and for each respective input type.

Figure 18A:
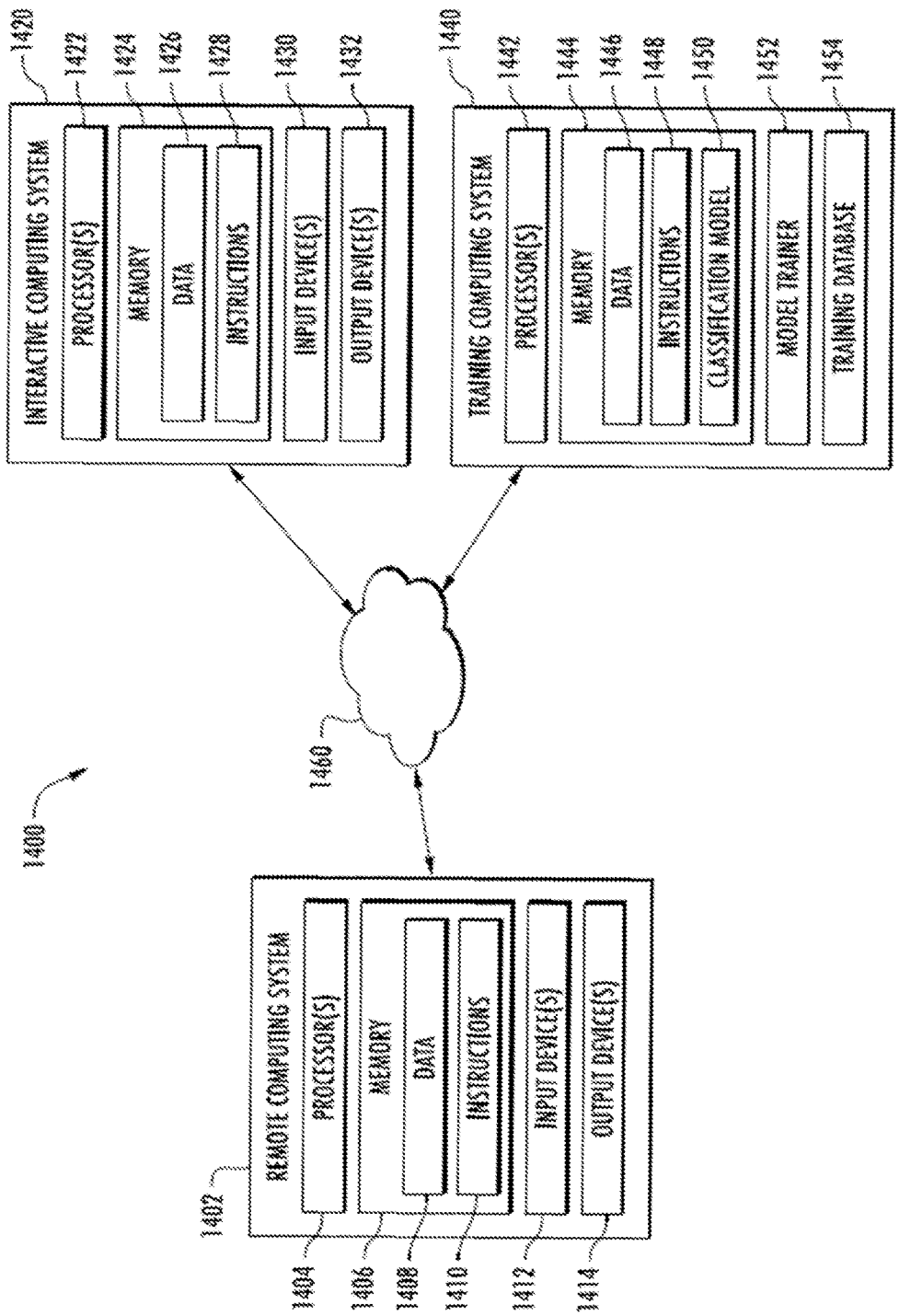
FIG. 18A depicts a block diagram of an example computing system that performs determining an audio feedback based on activity data and input data according to example embodiments of the present disclosure.

FIG. 18A depicts a block diagram of an example computing environment 1400 that can be used to implement any type of computing device as described herein. The system environment includes a remote computing system 1402, an interactive computing system 1420, and a training computing system 1440 that are communicatively coupled over a network 1460. The interactive computing system 1420 can be used to implement an interactive object in some examples.

The remote computing system 1402 can include any type of computing device, such as, for example, a personal computing device (e.g., laptop or desktop), a mobile computing device (e.g., smartphone or tablet), a gaming console or controller, an embedded computing device, a server computing device, or any other type of computing device.

The remote computing system 1402 includes one or more processors 1404 and a memory 1406. The one or more processors 1404 can be any suitable processing device (e.g., a processor core, a microprocessor, an ASIC, a FPGA, a controller, a microcontroller, etc.) and can be one processor or a plurality of processors that are operatively connected. The memory 1406 can include one or more non-transitory computer-readable storage mediums, such as RAM, ROM, EEPROM, EPROM, flash memory devices, magnetic disks, etc., and combinations thereof. The memory 1406 can store data 1408 and instructions 1410 which are executed by the processor 1404 to cause the remote computing system 1402 to perform operations.

The remote computing system 1402 can also include one or more input devices 1412 that can be configured to receive user input. By way of example, the one or more input devices 1412 can include one or more soft buttons, hard buttons, microphones, scanners, cameras, etc. configured to receive data from a user of the remote computing system 1402. For example, the one or more input devices 1412 can serve to implement a virtual keyboard and/or a virtual number pad. Other example user input devices 1412 include a microphone, a traditional keyboard, or other means by which a user can provide user input.

The remote computing system 1402 can also include one or more output devices 1414 that can be configured to provide data to one or more users. By way of example, the one or more output device(s) 1414 can include a user interface configured to display data to a user of the remote computing system 1402. Other example output device(s) 1414 include one or more visual, tactile, and/or audio devices configured to provide information to a user of the remote computing system 1402.

The interactive computing system 1420 can be used to implement any type of interactive object such as, for example, a wearable computing device. The interactive computing system 1420 includes one or more processors 1422 and a memory 1424. The one or more processors 1422 can be any suitable processing device (e.g., a processor core, a microprocessor, an ASIC, a FPGA, a controller, a microcontroller, etc.) and can be one processor or a plurality of processors that are operatively connected. The memory 1424 can include one or more non-transitory computer-readable storage mediums, such as RAM, ROM, EEPROM, EPROM, flash memory devices, magnetic disks, etc., and combinations thereof. The memory 1424 can store data 1426 and instructions 1428 which are executed by the processor 1422 to cause the interactive computing system 1420 to perform operations.

The interactive computing system 1420 can also include one or more input devices 1430 that can be configured to receive user input. For example, the user input device 1430 can be a touch-sensitive component (e.g., a touch sensor 102) that is sensitive to the touch of a user input object (e.g., a finger or a stylus). As another example, the user input device 1430 can be an inertial component (e.g., inertial measurement unit 158) that is sensitive to the movement of a user. Other example user input components include a microphone, a traditional keyboard, or other means by which a user can provide user input. The interactive computing system 1420 can also include one or more output devices 1432 configured to provide data to a user. For example, the one or more output devices 1432 can include one or more visual, tactile, and/or audio devices configured to provide the information to a user of the interactive computing system 1420.

The training computing system 1440 includes one or more processors 1442 and a memory 1444. The one or more processors 1442 can be any suitable processing device (e.g., a processor core, a microprocessor, an ASIC, a FPGA, a controller, a microcontroller, etc.) and can be one processor or a plurality of processors that are operatively connected.

The memory 1444 can include one or more non-transitory computer-readable storage mediums, such as RAM, ROM, EEPROM, EPROM, flash memory devices, magnetic disks, etc., and combinations thereof. The memory 1444 can store data 1446 and instructions 1448 which are executed by the processor 1442 to cause the training computing system 1440 to perform operations. In some implementations, the training computing system 1440 includes or is otherwise implemented by one or more server computing devices.

The training computing system 1440 can include a model trainer 1452 that trains a machine-learned classification model 1450 using various training or learning techniques, such as, for example, backwards propagation of errors. In other examples as described herein, training computing system 1440 can train machine-learned classification model 1450 using training data 1454. For example, the training data 1454 can include labeled sensor data generated by interactive computing system 1420. The training computing system 1440 can receive the training data 1454 from the interactive computing system 1420, via network 1460, and store the training data 1454 at training computing system 1440. The machine-learned classification model 1450 can be stored at training computing system 1440 for training and then deployed to remote computing system 1402 and/or the interactive computing system 1420. In some implementations, performing backwards propagation of errors can include performing truncated backpropagation through time. The model trainer 1452 can perform a number of generalization techniques (e.g., weight decays, dropouts, etc.) to improve the generalization capability of the classification model 1450.

In particular, the training data 1454 can include a plurality of instances of sensor data, where each instance of sensor data has been labeled with ground truth inferences such as one or more predefined movement recognitions. For example, the label(s) for each instance of sensor data can describe the position and/or movement (e.g., velocity or acceleration) of an object movement. In some implementations, the labels can be manually applied to the training data by humans. In some implementations, the machine-learned classification model 1450 can be trained using a loss function that measures a difference between a predicted inference and a ground-truth inference.

The model trainer 1452 includes computer logic utilized to provide desired functionality. The model trainer 1452 can be implemented in hardware, firmware, and/or software controlling a general purpose processor. For example, in some implementations, the model trainer 1452 includes program files stored on a storage device, loaded into a memory and executed by one or more processors. In other implementations, the model trainer 1452 includes one or more sets of computer-executable instructions that are stored in a tangible computer-readable storage medium such as RAM hard disk or optical or magnetic media.

In some examples, a training database 1456 can be stored in memory on an interactive object, removable electronics module, user device, and/or a remote computing device. For example, in some embodiments, a training database 1456 can be stored on one or more remote computing devices such as one or more remote servers. The machine-learned classification model 1450 can be trained based on the training data in the training database 1456. For example, the machine-learned classification model 1450 can be learned using various training or learning techniques, such as, for example, backwards propagation of errors based on the training data from training database 1456.

In this manner, the machine-learned classification model 1450 can be trained to determine at least one of a plurality of predefined movement(s) associated with the interactive object based on movement data.

The machine-learned classification model 1450 can be trained, via one or more machine learning techniques using training data. For example, the training data can include movement data previously collected by one or more interactive objects. By way of example, one or more interactive objects can generate sensor data based on one or more movements associated with the one or more interactive objects. The previously generated sensor data can be labeled to identify at least one predefined movement associated with the touch and/or the inertial input corresponding to the sensor data. The resulting training data can be collected and stored in a training database 1456.

The network 1460 can be any type of communications network, such as a local area network (e.g., intranet), wide area network (e.g., Internet), or some combination thereof and can include any number of wired or wireless links. In general, communication over the network 1460 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 18A illustrates one example computing system that can be used to implement the present disclosure. Other computing systems can be used as well. For example, in some implementations, the remote computing system 1402 can include the model trainer 1452 and the training data 1454. In such implementations, the classification model 1450 can be trained and used locally at the remote computing system 1402. In some of such implementations, the remote computing system 1402 can implement the model trainer 1452 to personalize the classification model 1450 based on user-specific movements.

Figure 18B:
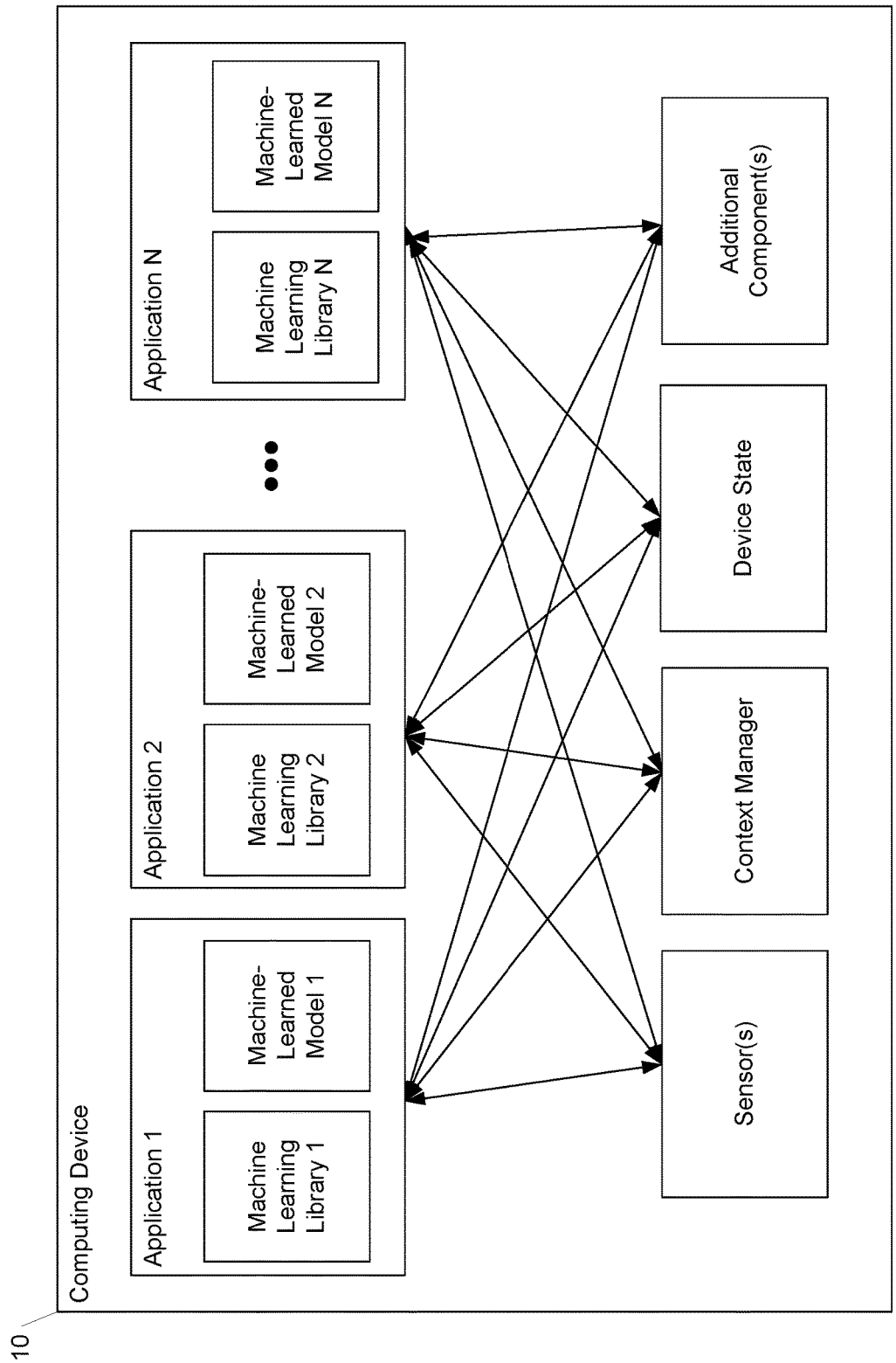
FIG. 18B depicts a block diagram of an example computing device that performs determining an audio feedback based on activity data and input data according to example embodiments of the present disclosure.

FIG. 18B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 18B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 18C:
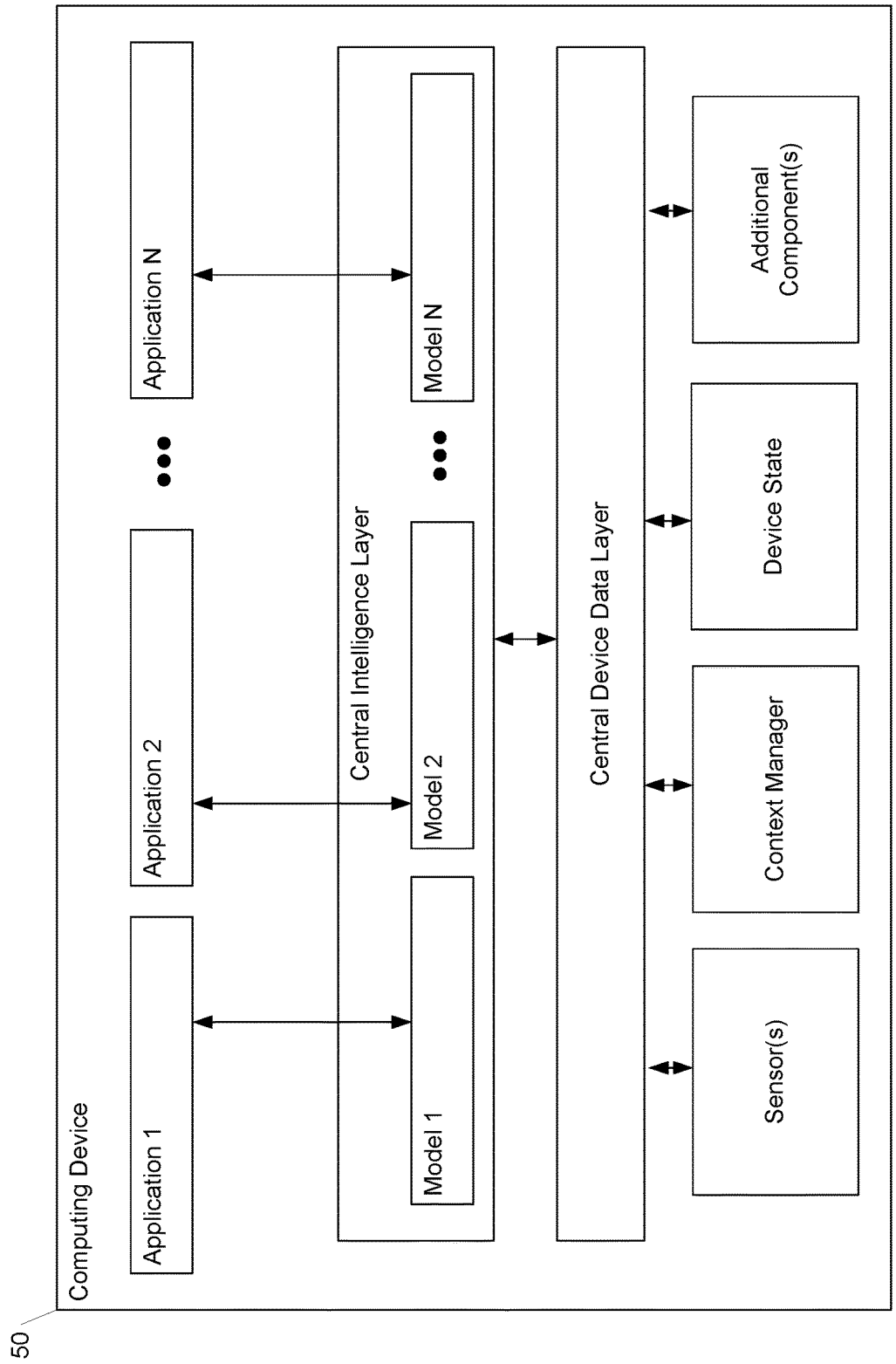
FIG. 18C depicts a block diagram of an example computing device that performs determining an audio feedback based on activity data and input data according to example embodiments of the present disclosure.

FIG. 18C depicts a block diagram of an example computing device 50 that performs according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 18C, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 18C, the central device data layer can communicate with a number of other components of the computing device, such as, for example, one or more sensors, a context manager, a device state component, and/or additional components. In some implementations, the central device data layer can communicate with each device component using an API (e.g., a private API).

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system for an interactive object, the system comprising:
    an input sensor;
    one or more activity sensors configured to generate activity data associated with user activity, wherein the one or more activity sensors comprise a location sensor;
    one or more control circuits configured to:
        determine an activity state of the user based at least in part on the activity data generated by the one or more activity sensors, wherein the activity state is determined based on location data generated by the location sensor, wherein the activity state is associated with a location, wherein the location is associated with a sound category;
        determine a gesture validity associated with at least one input detected by the input sensor;
        determine an audio feedback based at least in part on the activity state and the gesture validity, wherein the audio feedback is associated with the sound category, wherein the sound category of the audio feedback differs based on a user location, wherein the audio feedback comprises a first audio in the sound category when a gesture is valid, and wherein the audio feedback comprises a second audio in the sound category when the gesture is invalid;
        determining a particular action set based on the activity state, wherein the particular action set is determined based on historical data, wherein the historical data is descriptive of actions previously selected during the activity state;
        performing a particular action from the particular action set; and
    one or more audio output devices configured to provide the audio feedback based at least in part on the activity state and the gesture validity.

2. The system of claim 1, wherein the one or more control circuits are further configured to:
    determine a respective gesture set associated with the particular action set.

3. The system of claim 2, wherein the gesture validity is determined based on the input data and the respective gesture set.

4. The system of claim 2, wherein a first gesture set associated with a first action set differs from a second gesture set associated with a second action set.

5. The system of claim 1, wherein the input sensor comprises one or more touch sensors, and wherein the input data is descriptive of a gesture.

6. The system of claim 1, wherein the location comprises at least one of a library, a user house, a user workplace, or a commute of a user.

7. The system of claim 1, wherein the one or more control circuits are further configured to: provide haptic feedback based on the activity state.

8. The system of claim 1, wherein the one or more control circuits are further configured to: provide haptic feedback based on the gesture validity.

9. The system of claim 1, wherein the interactive object comprises a smart watch.

10. A computer-implemented method, the method comprising:
    obtaining, by a computing system comprising one or more processors, input data associated with at least one input detected by an input sensor;
    determining, by the computing system, an activity state of a user based at least in part on activity data generated by one or more activity sensors, wherein the one or more activity sensors configured to generate activity data associated with user activity, wherein the one or more activity sensors comprise a location sensor, wherein the activity state is determined based on location data generated by the location sensor, wherein the activity state is associated with a location, wherein the location is associated with a sound category;
    determining, by the computing system, a gesture validity associated with the at least one input detected by the input sensor;

determining, by the computing system, an audio feedback based at least in part on the activity state and the gesture validity, wherein the audio feedback is associated with the sound category, wherein the sound category of the audio feedback differs based on a user location, wherein the audio feedback comprises a first audio in the sound category when a gesture is valid, and wherein the audio feedback comprises a second audio in the sound category when the gesture is invalid;

determining, by the computing system, a particular action set based on the activity state, wherein the particular action set is determined based on historical data, wherein the historical data is descriptive of actions previously selected during the activity state;

performing, by the computing system, a particular action from the particular action set; and providing, by the computing system and via one or more audio output devices, the audio feedback based at least in part on the activity state and the gesture validity.

11. The method of claim 10, further comprising:

determining, by the computing system, a line-specific audio feedback for each touch sensor of the input sensor associated with the at least one input; and sending, by the computing system, a set of instructions to the one or more audio output devices to provide the line-specific audio feedback for each of a plurality of touch sensors associated with the at least one input.

12. The method of claim 11, wherein the line-specific audio feedback for each touch sensor is of a different sound frequency.

13. The method of claim 10, wherein the computing system comprises a smart wearable, wherein the smart wearable comprises the input sensor.

14. The method of claim 10, wherein the computing system comprises a smart wearable, wherein the smart wearable comprises the one or more activity sensors.

15. An interactive object, comprising:

an article having one or more touch sensors integrated therein for recognizing a user gestural input, wherein the one or more touch sensors comprise a plurality of conductive lines;

an electronic device associated with the article, the electronic device being communicatively coupled to the one or more touch sensors of the article, the electronic device having a processor and an audio output device capable of providing audio feedback to the user; and one or more activity sensors associated with at least one of the article or the electronic device, the one or more activity sensors comprises a location sensor;

wherein the electronic device is configured and programmed to:

determine an activity state of the user based at least in part on activity data generated by the one or more activity sensors, wherein the activity state is determined based on location data generated by the location sensor, wherein the activity state is associated with a location, wherein the location is associated with a sound category;

determine a gesture validity associated with at least one input detected by the one or more touch sensors;

determine an audio feedback based at least in part on the activity state and the gesture validity, wherein the audio feedback is associated with the sound category, wherein the sound category is associated with a particular music category, wherein a particular music category of the audio feedback differs based on a user location, wherein the audio feedback comprises a first audio in the particular music category when a gesture is valid, and wherein the audio feedback comprises a second audio in the particular music category when the gesture is invalid;

determining a particular action set based on the activity state, wherein the particular action set is determined based on historical data, wherein the historical data is descriptive of actions previously selected during the activity state;

performing a particular action from the particular action set; and one or more audio output devices configured to provide the audio feedback based at least in part on the activity state and the gesture validity.

16. The interactive object of claim 15, wherein the at least one input comprises a gesture, wherein the gesture comprises at least one of a touch gesture, a tap gesture, a swipe gesture, a hold gesture, or a stroke gesture.

17. The interactive object of claim 15, wherein the one or more touch sensors are integrated within a flexible object.

18. The interactive object of claim 15, wherein the interactive object comprises computing spectacles.

19. The interactive object of claim 15, further comprising:

determining that a user activity state changes from a first activity state to a second activity state;

determining an activity state sound associated with the second activity state; and sending activity state instructions to the one or more audio output devices to play the activity state sound.

* * * * *